United States Patent
Tanabata et al.

(10) Patent No.: US 7,499,573 B2
(45) Date of Patent: Mar. 3, 2009

(54) PLANT GROWING ANALYZING SYSTEM AND METHOD

(75) Inventors: Takanari Tanabata, Saitama (JP); Tomoko Shinomura, Higashimatsuyama (JP); Toru Ishizuka, Higashikurume (JP); Masafumi Kanetomo, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 942 days.

(21) Appl. No.: 10/887,931

(22) Filed: Jul. 12, 2004

(65) Prior Publication Data

US 2005/0180608 A1 Aug. 18, 2005

(30) Foreign Application Priority Data

Feb. 17, 2004 (JP) .............................. 2004-039497

(51) Int. Cl.
*G06K 9/00* (2006.01)
(52) U.S. Cl. ...................................... 382/110; 382/294
(58) Field of Classification Search ................. 382/110, 382/152, 294
See application file for complete search history.

(56) References Cited

U.S. PATENT DOCUMENTS

| | | | | |
|---|---|---|---|---|
| 5,253,302 A | * | 10/1993 | Massen | 382/110 |
| 6,429,016 B1 | * | 8/2002 | McNeil | 436/47 |
| 6,514,372 B1 | * | 2/2003 | Yamazaki | 156/256 |
| 6,537,801 B1 | | 3/2003 | Ida et al. | |
| 7,123,750 B2 | * | 10/2006 | Lu et al. | 382/110 |

| | | | |
|---|---|---|---|
| 2002/0146347 A1 | | 10/2002 | McNeil |

FOREIGN PATENT DOCUMENTS

| EP | 0 390 192 A1 | 3/1990 |
|---|---|---|
| JP | 6-138041 | 10/1992 |
| JP | 9-224481 | 2/1996 |
| JP | 11-110530 | 10/1997 |
| JP | 60-83597 | 8/2001 |
| JP | 2003-47340 | 8/2001 |
| JP | 2003-50996 | 8/2001 |

OTHER PUBLICATIONS

"The Rice Growth Monitoring System for The Phenotypic Functional Analysis", 10 pages, http://www.gs.dna.affrc.go.jp/SY-1108/.

(Continued)

*Primary Examiner*—John B Strege
(74) *Attorney, Agent, or Firm*—Reed Smith LLP; Juan Carlos A. Marquez, Esq.

(57) ABSTRACT

There are provided an image acquisition system capable of storing high-accuracy measurement of changes in the shape of a plant growing process in image information with high accuracy and an analyzing method for analyzing an acquired image to analyze plant growing.

There is provided a plant growing analyzing system having operation detection means of a conveying mechanism of a plant in order that an observed plant in an image is photographed at a constantly fixed position or angle; a position detecting mark in the acquired image; a computation part for evaluating detected data to control a conveying amount; and a conveying control part, wherein the growing process of many plants is stored in image information in a long period, and the stored image is used to realize high-accuracy measurement.

17 Claims, 33 Drawing Sheets

OTHER PUBLICATIONS

European Search Report dated Jun. 27, 2005.
Takanari Tanabata et al., "Intelligent Systems for Molecular Biology", 10th International Conference, presented by International Society for Computational Biology, Aug. 3-7, 2002, Edmonton, Alberta, Canada.
Takanari Tanabata et al., "Imaging System in Gene Functional Analysis", Proceedings of Institute of Electronics, Information and Communication Engineers, vol. 86, No. 12, pp. 945-948, with 8 pages of English translation.
Toru Ishizuka et al., "Development of Rice Growth Imaging System", The 26th Annual Meeting of the Molecular Biology Society of Japan, Dec. 10-13, 2003, Kobe, Japan, pp. 1011, with 2 pages of English translation.
Toru Ishizuka et al., "Rice Growth Imaging System for Phenotypic Functional Analysis from Middle Seedling to Mature Plant", Proceedings of International Genetic Resources Workshop on the Genus Oryza, Sep. 24-26, 2003, Tsukuba, Japan, pp. 81-83.
Takanari Tanabata et al. "The Rice Growth Monitoring System for the Phenotypic Functional Analysis", web published article (Aug. 16, 2003), http://www.gs.dna.affrc.go.jp/SY-1108/, 2 pages.
"TraitMill—Platform and Process", web published article (Apr. 19, 2004), http://www.cropdesign.com.

* cited by examiner

FIG.5B

| OPERATION ORDER | CONTROLLED TARGETS | EXTERNAL DEVICE CONTROL | | | | |
|---|---|---|---|---|---|---|
| | | MOTOR A | MOTOR B | ILLUMINATION | | CAMERA |
| 1 | CONVEYING MECHANISM | ON | OFF | OFF | | OFF |
| 2 | ONE-SECOND WAIT | OFF | OFF | OFF | | OFF |
| 3 | TURNING ON ILLUMINATION | OFF | OFF | ON | | OFF |
| 4 | IMAGE CAPTURING | OFF | OFF | ON | | OFF |
| .. | | .. | .. | .. | | .. |
| n | END | OFF | OFF | OFF | | OFF |

1016

| No. | OPERATION DATES | MOTOR OPERATION AMOUNTS | | TABLE MOVEMENT AMOUNTS |
|---|---|---|---|---|
| | | MOTOR A | MOTOR B | |
| 0 | x/x/x  x:x:x | 20.0 | 25.0 | 301.25 |
| : | : | : | : | : |
| n | y/y/y  y:y:y | 20.9 | 24.8 | 300.55 |

$T_0 (x_0, y_0)$    $T_1 (x_1, y_1)$    $T_2 (x_2, y_2)$    $T_3 (x_3, y_3)$    $T_4 (x_4, y_4)$

COORDINATES $T_i (=0, 1, ...)$ OF DETECTED MARK CENTER

| No. | OPERATION DATES | MOTOR OPERATION AMOUNTS | | TABLE MOVEMENT AMOUNTS | MARK DETECTION COORDINATE VALUES |
|---|---|---|---|---|---|
| | | MOTOR A | MOTOR B | | $T_i (x_i, y_i)$ |
| 0 | x/x/x x:x:x | 20.0 | 25.0 | 301.25 | (100, 100) |
| ⋮ | ⋮ | ⋮ | ⋮ | ⋮ | ⋮ |
| n | y/y/y y:y:y | 20.9 | 24.8 | 300.55 | (101, 101) |

FIG.13B

| No. | CONTENTS OF OPERATIONS | DEVICE OPERATION AMOUNTS | | | CHECKED DATA AFTER OPERATION | |
|---|---|---|---|---|---|---|
| | | MOTOR OPERATION AMOUNTS | | TABLE MOVEMENT AMOUNTS | TABLE POSITIONS | MARK DETECTION COODINATE VALUES |
| | | MOTOR A | MOTOR B | | | $T_i (x_i, y_i)$ |
| 0 | INITIALIZATION | 180.0 | 180.0 | 360.00 | 0.0 | (0, 0) |
| 1 | TEST OPERATION 1 | 230.0 | 200.0 | 430.0 | 70.0 | (200, 100) |
| 2 | SAMPLE CONVEYING 1 | 10.0 | 10.0 | 12.0 | 12.0 | (100, 100) |
| .. | .. | .. | .. | .. | .. | .. |

FIG.14A

| SAMPLE No. | CAPTURING DATES | EXPERIMENTAL CONDITIONS | | | STORED FILE NAMES |
|---|---|---|---|---|---|
| | | TEMPERATUES | ... | HUMIDITIES | |
| 0 | yy/m/d h:m:s | 28.1 | | 76.0 | yy-m-d-h-m-s.bmp |
| | : | : | : | : | : |
| | yy/m/d h:m:s | 27.9 | | 76.1 | yy-m-d-h-m-s.bmp |
| 1 | yy/m/d h:m:s | 28.2 | | 77.0 | yy-m-d-h-m-s.bmp |
| | : | : | : | : | : |
| | yy/m/d h:m:s | 27.8 | | 78.3 | yy-m-d-h-m-s.bmp |
| : | : | : | : | : | : |

FIG. 14B

| SAMPLE No. | EXPERIMENTAL CONDITIONS | | | | STORED FILE NAMES | ANALYZED DATA | | |
|---|---|---|---|---|---|---|---|---|
| | CAPTURING DATES | TEMPERATURES | ... | HUMIDITIES | | LENGTHS [mm] | ANGLES [DEGREES] | GROWING SPEEDS |
| 0 | yy/m/d h:m:s | 28.1 | | 76.0 | yy-m-d-h-s.bmp | 8.9 | 0.5 | 2.5 |
| | .. | .. | | .. | .. | .. | .. | .. |
| | yy/m/d h:m:s | 27.9 | | 76.1 | yy-m-d-h-s.bmp | 20.5 | 2.02 | 4.0 |
| 1 | yy/m/d h:m:s | 28.2 | | 77.0 | yy-m-d-h-s.bmp | 7.6 | 0.1 | 1.3 |
| | .. | .. | | .. | .. | .. | .. | .. |
| | yy/m/d h:m:s | 27.8 | | 78.3 | yy-m-d-h-s.bmp | 22.3 | 32.2 | 3.9 |
| .. | .. | .. | | .. | .. | .. | .. | .. |

MOVEMENT DIRECTION

MOVEMENT DIRECTION

PLANT GROWING ANALYZING SYSTEM AND METHOD

CLAIM OF PRIORITY

The present application claims priority from Japanese application JP 2004-039497 filed on Feb. 17, 2004, the content of which is hereby incorporated by reference into this application.

FIELD OF THE INVENTION

The present invention relates to a system for analyzing changes in the state in a plant growing process.

BACKGROUND OF THE INVENTION

There has been advanced plant phenotypic functional analysis which observes the growing of a plant having changed noted genetic information in a gene arrangement by changing environmental conditions (e.g., sunshine duration), measures the difference in change in the form in a growing process, the leaves or the overall shape of the mature plant, and the difference in the color of the leaves or root, and specifies a phenotypic function from the results.

In recent years, an enormous amount of plant genetic information has been clarified to advance functional analysis for the obtained enormous amount of genetic information. It is important to make all-inclusive measurement throughout a growing process including even small changes difficult to discriminate by human eyes in the shape, the color difference and the changed state in the growing process.

In growing process measurement, a growing process when changing genetic information and environmental conditions has been observed by a measuring work at fixed intervals, e.g., once a day or once per a few days. In manual measurement, there is performed growing storing of noted points of an observed object, such as the length of a root, the size of leaves and a growing angle, which are easily quantified. In this case, there is typically performed a measurement method of making measurement at long-period intervals, e.g., one day or more, to note large changes. Actually, studies of experiments using such method have been advanced and their results have been shown in the form of theses or presentation at conferences.

As a method of automatically performing growing storing, there is an image monitoring system using a camera. Patent Document 1 (Japanese Patent Application Laid-Open No. Hei 6-138041) proposes a system for monitoring whether the growing state of a plant is good or poor. This system captures an image of the growing state of a seedling using a camera, evaluates the captured image, and automatically determines whether the growing state is good or poor.

As an automatic storage system using a camera, there is a field monitoring a suspicious person or object, although the field of a photographed object is different. In the monitoring field, there is proposed, in order to determine a suspicious person or object, a system which captures an image of a monitored area at fixed intervals or continuously using a camera, evaluates differential information on some adjacent images in capturing time by image processing, and gives an alarm when any change occurs.

As the proposal of a monitoring system, there is Patent Document 2 (Japanese Patent Application Laid-Open No. Hei 11-110530). This proposes that changes in images chronologically captured are evaluated, and the storing intervals of the images are dynamically changed based on the evaluated value to reduce the storage capacity of the images. Such monitoring system evaluates two or some images before and after capturing time which are handled for evaluating changes in shape and uses captured images in a relatively short time such as a few hours or a few minutes. The influence of an operation error of a camera or changes in angle of an object due to vibration of a stage fixing the camera or the system itself is less.

The growing monitoring system of Patent Document 1 proposes that comparison with a previously known plant growing process is performed to determine as compared with a previously known growing state whether a growing state is good or poor.

Non-Patent Documents 1-5 propose systems conveying cases for growing plants to sequentially capture images taken out before a camera.

Patent Document 3 (Japanese Patent Application Laid-Open No. 2003-50996) proposes that a position detecting mark is attached to a case growing a plant in photographing, the mark position in a captured image is detected, and the image is corrected with reference to its physical position.

[Patent Document 1] Japanese Patent Application Laid-Open No. Hei 6-138041

[Patent Document 2] Japanese Patent Application Laid-Open No. Hei 11-110530

[Patent Document 3] Japanese Patent Application Laid-Open No. 2003-50996

[Non-Patent Document 1] Presentation at conference: Tanabata, T., Ishizuka, T., Takano, M., Shinomura, T., The rice growth monitoring system for the phenotypic functional analysis, The 10th International Conference on Intelligent Systems for Molecular Biology, Edmonton, Canada, proceedings p. 67, Aug. 3-7, 2002

[Non-Patent Document 2] Description articles of proceedings: Tanabata, T., Ishizuka, T., Shinomura, T., The imaging processing system for the phenotypic functional analysis, Proceedings of Institute of Electronics, Information and Communication Engineers, 86: 945-948, 2003.

[Non-Patent Document 3] Presentation at conference: Ishizuka, T., Tanabata, T., Shinomura, T., The development of the rice growth automatic monitoring system, The 26th Annual Meeting of The Molecular Biology Society of Japan, Program and speech summaries, p. 1011, 2003.

[Non-Patent Document 4] Presentation at conference: Ishizuka T, Tanabata T, and Shinomura T, Rice growth imaging system for phenotypic functional analysis from middle seedling to mature plant, Proceedings of International Genetic Resources Workshop on the Genus Oryza. pp. 81-83, 2003.

[Non-Patent Document 5] Web publicly-shown articles: Tanabata T., Ishizuka T., Shinomura T., The Rice Growth Monitoring System for The Phenotypic Functional Analysis, http://www.gs.dna.affrc.go.jp/SY-1108/, Aug. 16, 2003.

SUMMARY OF THE INVENTION

To obtain all information on a plant growing process, the prior art manual observation method may miss small differences and changes in the plant growing process. In addition, manual work being major, it takes a very long time to advance functional analysis for an enormous amount of genetic information. The labor cost for the analysis is very high.

As a method of solving the problems, there is proposed a method of storing growing with an image acquisition system using a camera to make shape measurement in a growing process based on collected images.

The growing monitoring system of Patent Document 1 only determines whether the growing state is good or poor and cannot obtain information in which part of the growing state is poor.

The present invention can realize providing an optimum photographing environment in capturing the growing images of a plurality of plants. A plant conveying mechanism observes a plant such as rice in which its shape is largely changed with its growth. The growing period is shifted for observation since the operation of the conveying mechanism is fixed. Large and small samples are conveyed at a time. In order not to overlap the plants with each other, the conveying operation must be performed according to the large samples. The conveying mechanism is larger for the small plants, thereby wasting its space.

When analyzing an unknown phenotypic function, this corresponds to the case of observing a plant whose growing state is quite unknown. When a plant is grown to be extremely large than expected, the conveying operation is performed at an expected value until the state is found by human. The human must check the state to change the conveying operation for acquiring optimum images. The perfect automation of the image acquisition system for growing analyzing is difficult by these methods.

To analyze a plant growing process, image acquisition of the growing process of many plants must be performed to compare the obtained plant growing images. For the comparison, in order to measure a factor other than changes in the growing of plants in photographing, e.g., their shape, a condition of the physical position relation of photographing between a camera and a plant is constantly fixed during the observation period, which is a very important item to maintain the measurement accuracy at high level.

To this problem, the present invention can realize reduction in error factor in measurement with the shift of the physical position relation between a camera and a plant due to an-operation error of a conveying mechanism caused during the operation of the conveying mechanism by using obtained images to correct the position relation between the images and increase in measurement accuracy. The growing monitoring system in Patent Document 1 can realize the above by processing only obtained images. In consideration of its application to phenotypic analysis, it is necessary to acquire images of an enormous amount of plants and to perform image acquisition using many image acquisition systems. In this case, when performing exact comparison with other samples for growing analyzing, it is important to perform the operation in image acquisition with high accuracy in order that physical position alignment of a camera and plants between images is strict.

An object of the present invention is to provide a plant growing analyzing system using an image acquisition system for phenotypic functional analysis which can stably store image information on changes in the growing process of a living thing including a plant with time including even small changes in a growing process in a long period from a few weeks to a few months or more, which is difficult by the prior art manual measurement and the mere application of a monitoring system and an analyzing method of efficiently performing growing analyzing using obtained images.

A plant growing analyzing system of the present invention has operation detection means of a mechanism conveying many observed objects to repeatedly pass a camera; means detecting an operation error of the conveying mechanism using images acquired by the camera; and conveying control means reflecting the amount of detected error of the conveying mechanism on the conveying mechanism to correct the operation, wherein a plant growing process in a long period is stored in image information to measure changes in the shape of growing with high accuracy.

The present invention permits image acquisition which can make various measurements of the size and color for chronological changes in the shape of a living thing including a plant in a long period with time at high-accuracy level.

The present invention provides a method of efficiently analyzing an acquired image and a method of phenotypic functional analysis of a living thing including small changes.

In image acquisition, a large amount of growing images of observed living things having different sizes can be efficiently acquired.

BRIEF DESCRIPTION OF THE DRAWINGS

FIG. 5B is a diagram showing an example of a data table 1016 stored in a sequence operation order storing part 1014 according to Embodiment 1;

FIG. 13B is a diagram showing an example of a data table of a conveying mechanism standard operation amount storing part 1026 according to Embodiment 1;

FIG. 14A is a diagram showing an example of data of an image information storing part 106 according to Embodiment 1;

FIG. 14B is a diagram showing an example of data of an analyzed result storing part 3 according to Embodiment 1;

DESCRIPTION OF THE PREFERRED EMBODIMENT

Embodiments of the present invention will be described below with reference to the drawings. Embodiment 1 describes an application to small observed plants growing in test tubes. Embodiment 2 describes an application to observed plants growing to be above 1 m.

Embodiment 1

Figure 1:
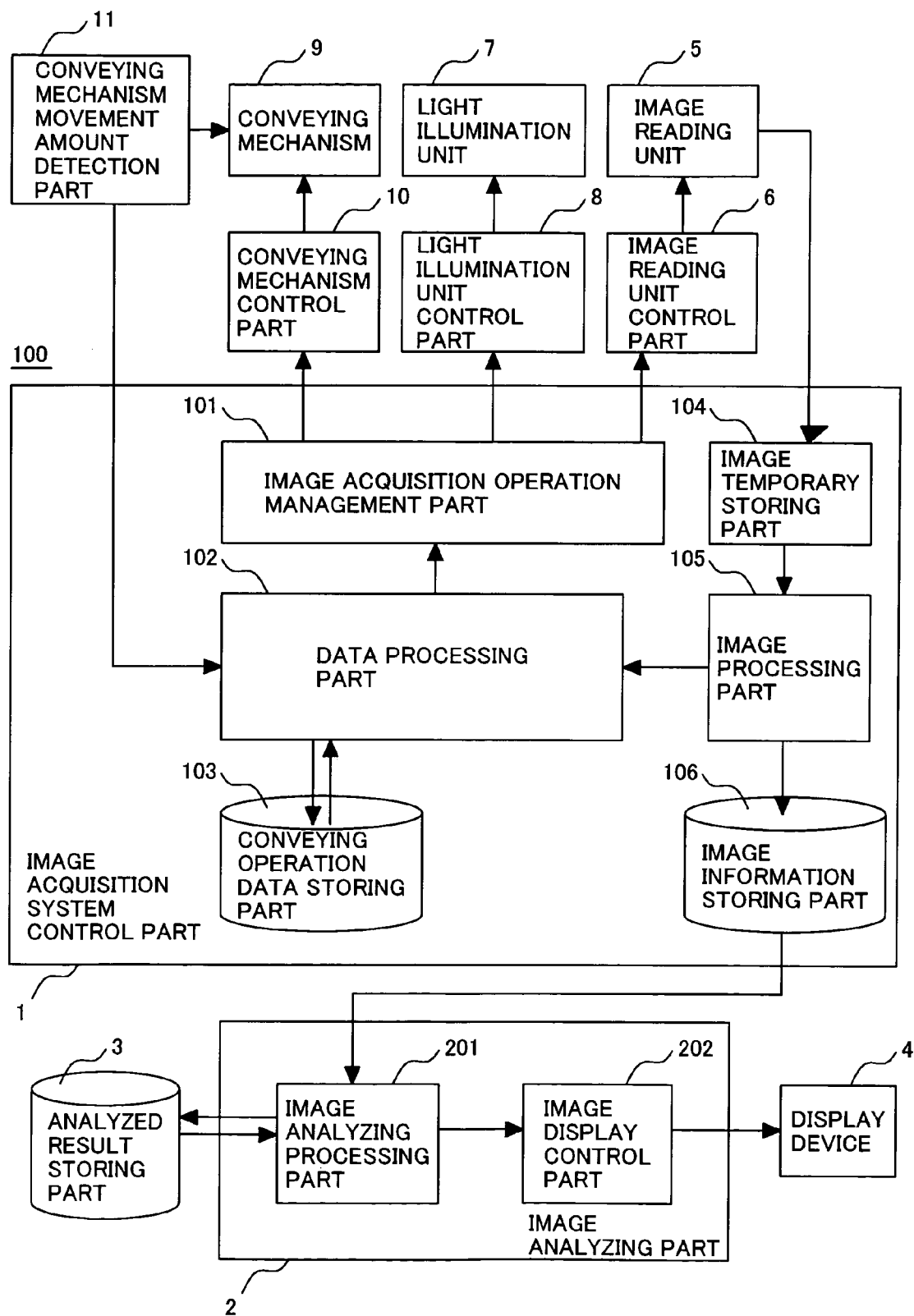
FIG. 1 is a diagram showing a functional block of a system according to the present invention.

FIG. 1 is a diagram showing a functional block of a system according to the present invention.

A plant growing analyzing system of the present invention has an image acquisition system 100 for acquiring images of a growing process in a long period having an image acquisition system control part 1, an image reading unit 5 for acquiring images, an image reading unit control part 6, light illumination unit 7 to be used as illumination in photographing, a light illumination unit control part 8, a conveying mechanism 9 for conveying a plurality of plants, a conveying mechanism control part 10, and a conveying mechanism movement amount detection part 11 for monitoring a conveying state; and an image analyzing part having an image analyzing processing part 201 for visualizing changes in shape and measuring the amounts of changes in shape to acquired images in order to compare changes in growing of various plants using the acquired images, an image display control part 202 for processing analyzed results to data to be displayed on a display device 4, an analyzed result storing part 3 for storing the analyzed results, and the display device 4 such as a display or printer displaying the analyzed results.

The image acquisition system control part 1 has an image acquisition operation management part 101, an image temporary storing part 104, an image processing part 105, an image information storing part 106, a data processing part 102, and a conveying operation data storing part 103. The image acquisition operation management part 101 gives a control signal to the image reading part control part 6, the light illumination means control part 8 and the conveying mechanism control part 10 by a signal given from the data processing part 102. An image signal obtained by the image reading part 5 is stored in the image temporary storing part 104 to be processed by the image processing part 105. The signal of the image processing part 105 is given to the data processing part 102 and is sent via the image information storing part 106 to the image analyzing processing part 201 to be analyzed according to a predetermined analyzing program. A signal obtained from the conveying mechanism movement amount detection part 11 is sent to the data processing part 102. The data processing part 102 is coupled to the conveying operation data storing part 103 to store the operation state of the conveying mechanism and transmits to the image acquisition operation management part 101 a signal to the conveying mechanism control part 10 according to a program signal to be given to the conveying mechanism control part 10 and the signal obtained from the conveying mechanism movement amount detection part 11.

The configurations of such image acquisition system and image analyzing part can realize obtaining and analyzing in images changes in growing in the growing process of many plants and differences in growing between the plants and displaying the results. The respective operations will be sequentially described.

Figure 2:
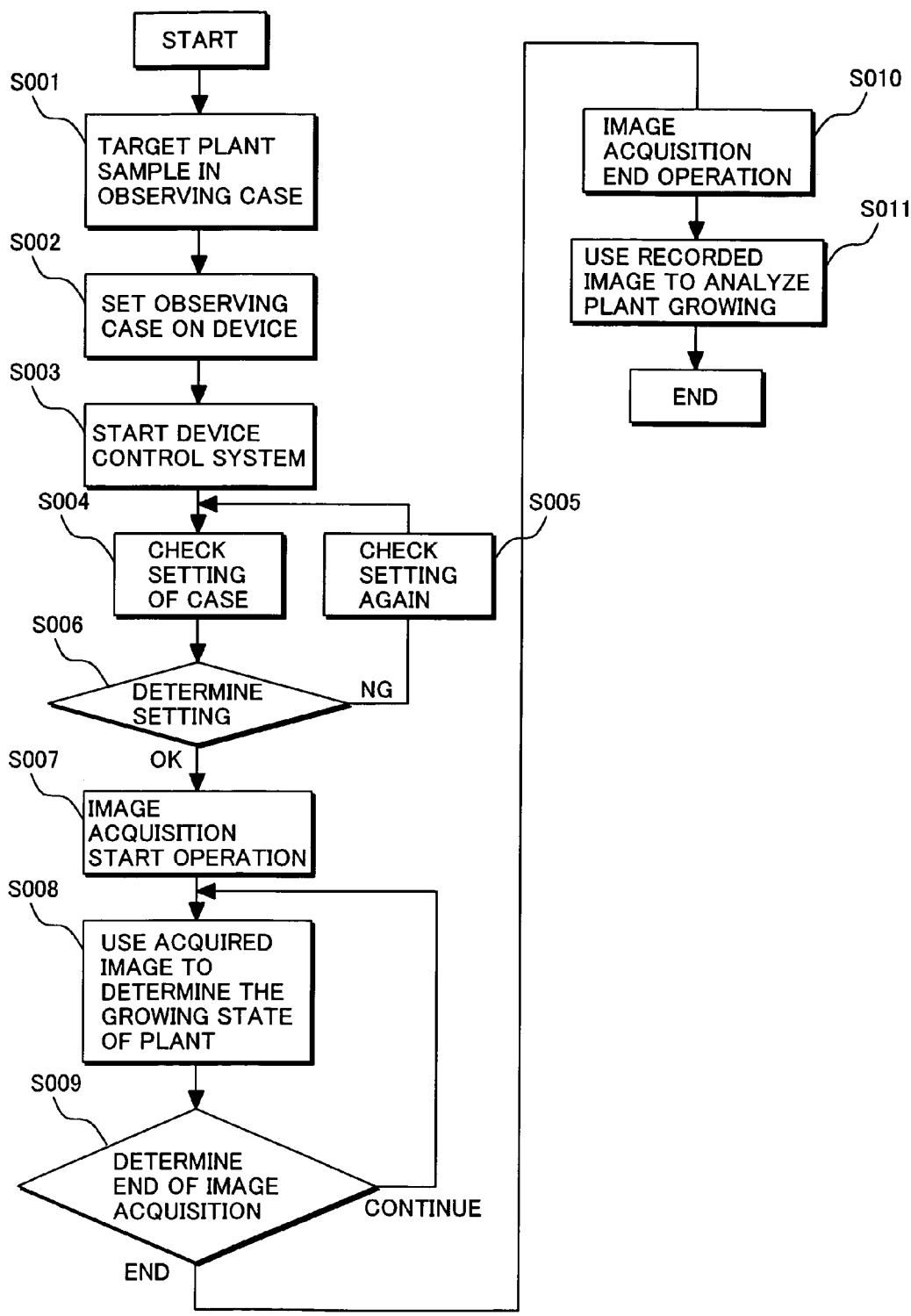
FIG. 2 is a flowchart showing a plant growing analyzing method using the system according to the present invention.

FIG. 2 is a flowchart showing a plant growing analyzing method using the system according to the present invention.

The seed or seedling of a plant for growing analyzing is planted in a growing case for growing the plant (S001). In this system, as described later, the conveying mechanism control part 10 performs automatic control of a conveying amount according to the size of the case so as to always realize optimum photographing. The size of the case is not limited. The growing case is set on the conveying mechanism 9 (S002). When the setting is completed, the image acquisition system 101 is started (S003). When it is ready, a test operation of the conveying mechanism 9 is performed to check the setting state of the case (S004). The test operation and check can be manually realized. A previously defined check operation is executed to monitor the operation state during that using a signal of the conveying mechanism movement amount detection part 11 and a signal of the image processing part 105, thereby automating the setting check. After the setting check (S004), the setting state is determined (S006). When the setting is incomplete, the setting state is checked again (S005) to perform the setting check (S004) again. This is repeated until the setting is completed.

After determination of the setting (S006) is completed, an image acquisition start operation is performed (S007). After starting image acquisition, an image of the plant is acquired at fixed intervals. The interval of image acquisition is previously specified to be once per a few minutes or once per a few hours and can be freely changed according to an object of growing analyzing. During the image acquisition period, the growing state of the plant is checked once a day or once a week (S008) to determine end of the image acquisition (S009). The check of the growing state can be also performed by a method of checking and determining an acquired image by human or be ended by automatically determining from an acquired image by the signal of the image processing part 105 that the plant is thickly grown in the case.

The signal of the image processing part 105 is used for automatic determination, which can realize complete automation of image acquisition and permits efficient image acquisition. After determination of end of image acquisition, an end operation (S010) is performed to execute plant growing analyzing using the acquired image (S011). The above operation flow can efficiently execute the processing from image acquisition of growing of the plant to growing analyzing using the acquired image.

Figure 3:
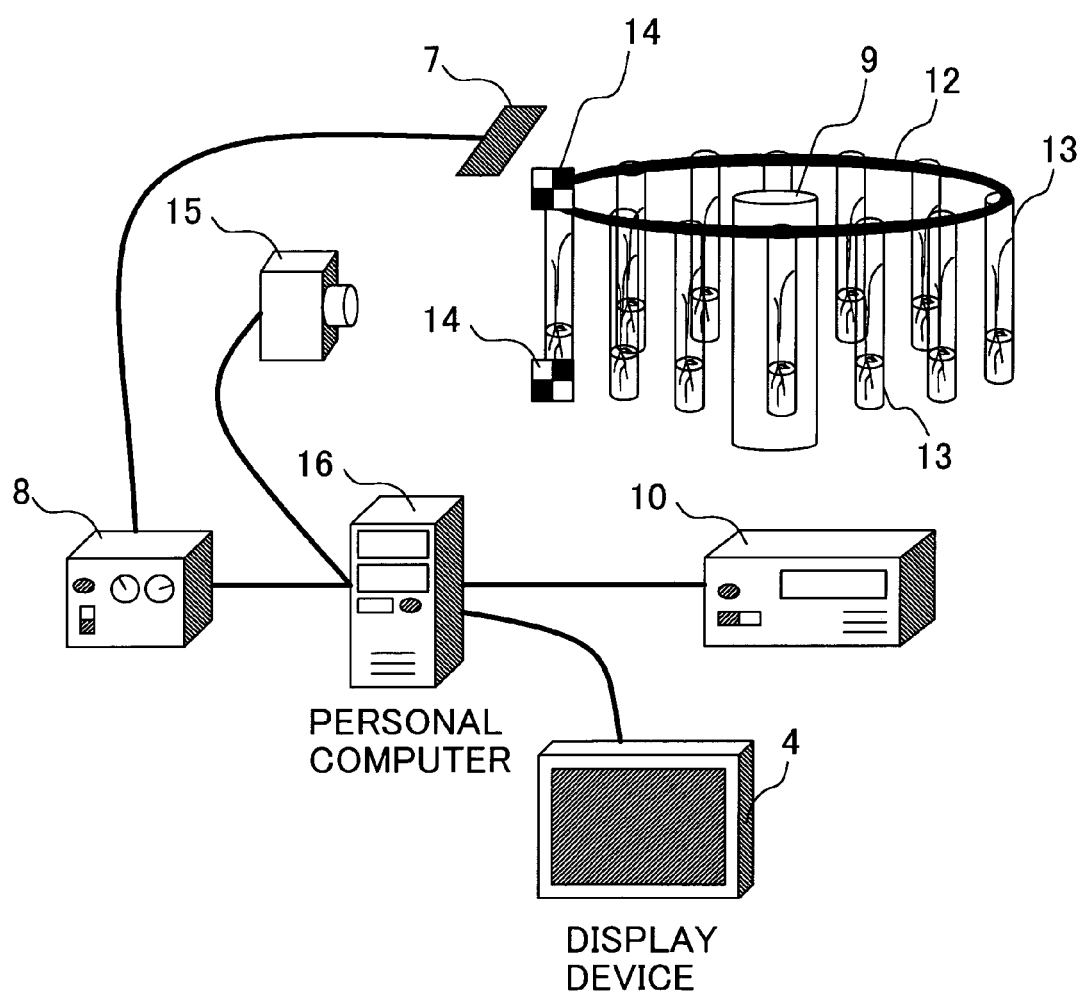
FIG. 3 is a schematic diagram of an embodiment of the system according to the present invention.

FIG. 3 is a schematic diagram of an embodiment of the system according to the present invention.

The conveying mechanism 9, in which the detail of an example thereof will be described later, many growing cases 13 are set on a ring 12 to be rotated and controlled by the conveying control part 10. These growing cases 13 are temporarily stopped before a camera 15 integrally housing the image reading part 5 not shown, and the image reading part control part 6, not shown, and image reading is performed. A later-described position detecting mark 14 is fixed on a predetermined position of each of the growing cases 13, although representatively, it is fixed onto only one of the growing cases 13 in the drawing. Image reading is performed together to an observed plant and the position detecting mark 14. In this case, as photographing illumination, the light illumination means 7 is provided above. As in this embodiment, the light illumination means 7 for illumination is provided above to reduce reflection light photographed in the image caused by the material of the growing case 13. The display device 4 displaying the acquired image and the analyzed results is connected to a personal computer 16.

In this embodiment, the image acquisition system control part 1 performing conveying mechanism control and image reading part control, the image analyzing part 2, and the analyzed result storing part 3 are realized by the software on the personal computer 16. Since they can be realized by software processing, the system configuration is simple and the system can be flexibly modified.

Figure 4A:
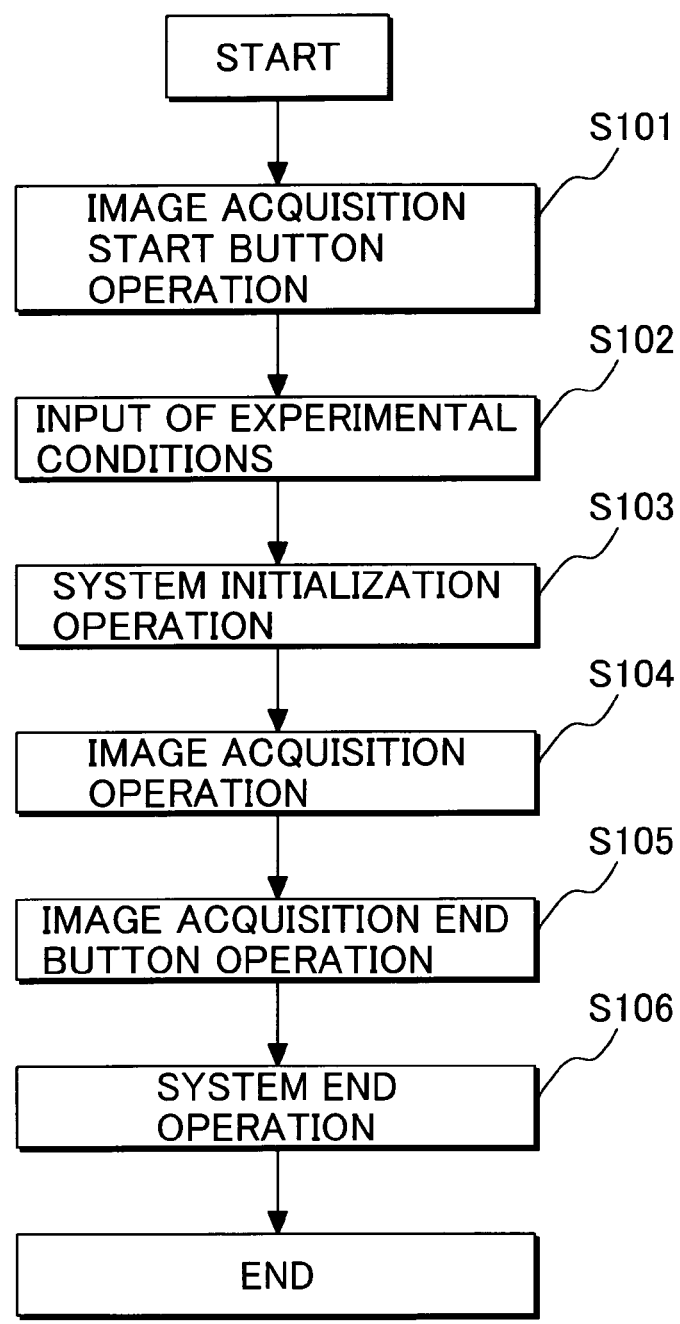
FIG. 4A is a diagram showing an operation flow of an image acquisition system control part according to Embodiment 1.
Figure 4B:
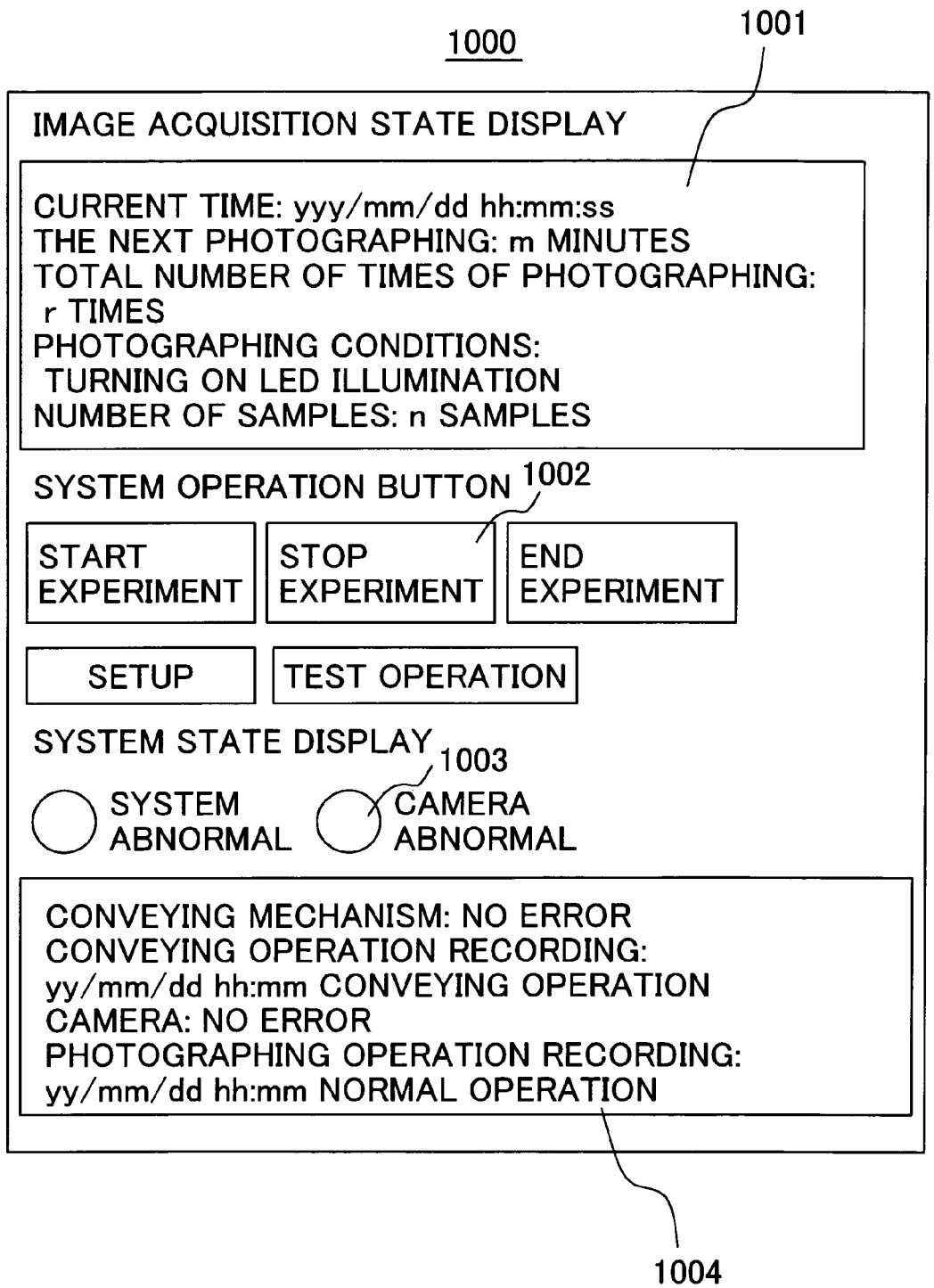
FIG. 4B is a diagram showing an example of the configuration of the console panel of the image acquisition system control part 1 according to Embodiment 1.

FIGS. 4A and 4B are diagrams showing the processing description of the image acquisition system control part 1.

FIG. 4A is a diagram showing an operation flow of the image acquisition system control part according to Embodiment 1. When the user performs an image acquisition start button operation (S101) after operation, displaying for setting experimental conditions (image acquisition conditions) by the user is performed (S102). The conditions are about an image acquisition operation such as acquisition time interval at which image acquisition is performed once per a few minutes and the number of plants set on the conveying mechanism. After inputting the conditions (S102), a system initializing processing operation (S103) for returning the operation initial position of the system is performed to start an image acquisition operation (S104). During the image acquisition operation, an image of the plant is acquired according to a time schedule specified at the input of the conditions (S102). When determining end of image acquisition, an end operation is performed (S106) to end the image acquisition.

FIG. 4B is a diagram showing an example of the configuration of the console panel of the image acquisition system control part 1 according to Embodiment 1. This example shows an embodiment of the software on the personal computer 16. A display screen 1000 of the console panel has operation buttons 1002 starting, stopping and ending the image acquisition operation and an optional conveying mechanism operation such as the test operation. It further has an image acquisition state display screen 1001 displaying the state of image acquisition such as the number of times of image photographing and photographing time, lamps 1003 indicating an alarm when the conveying mechanism or the camera are abnormal, and a system state display screen of display 1004 of the operation state of the conveying mechanism and the camera.

Figure 5A:
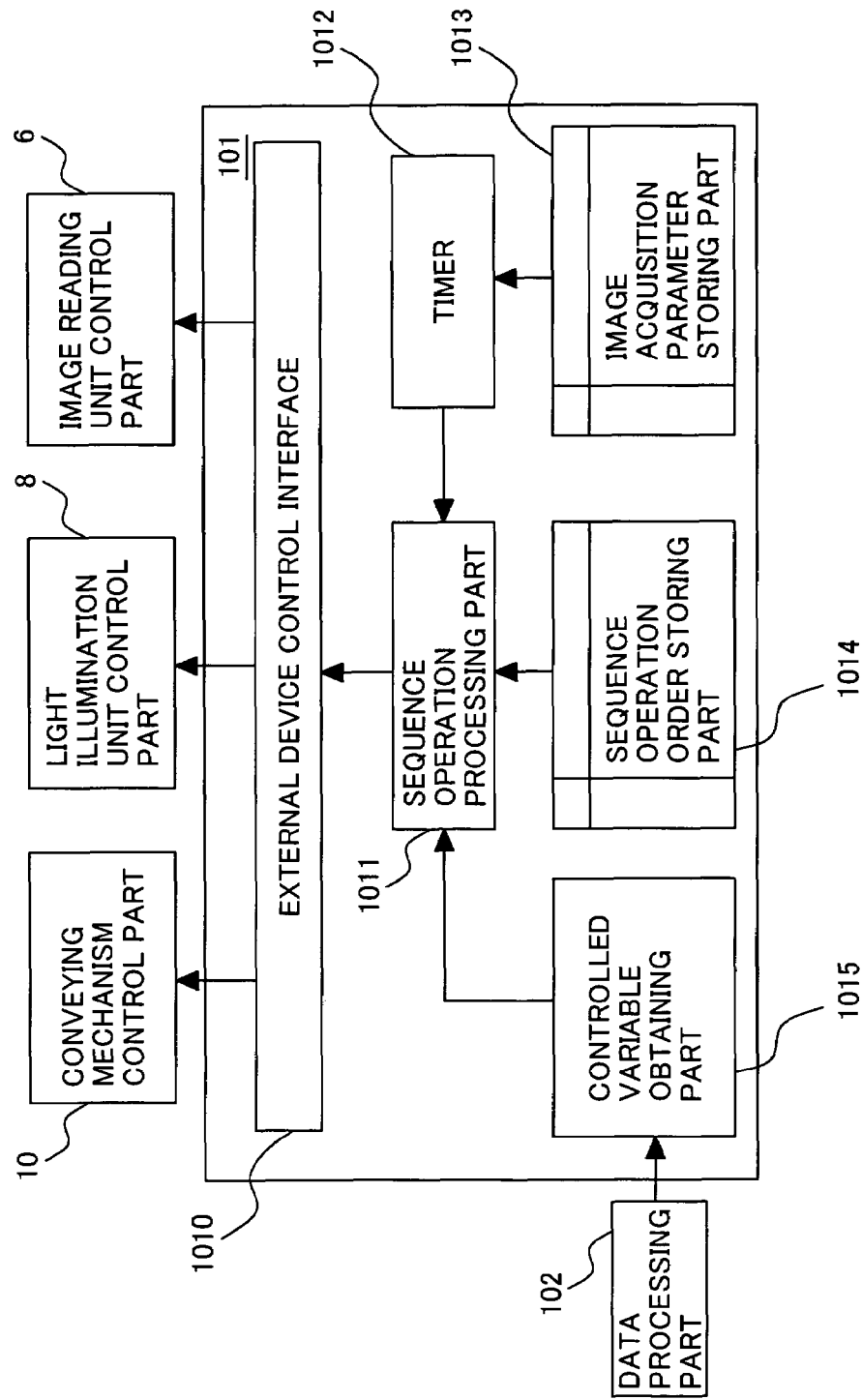
FIG. 5A is a diagram showing a functional block of an image acquisition operation management part 101 according to Embodiment 1.

FIGS. 5A and 5B are explanatory views of the image acquisition operation management part 101.

FIG. 5A is a diagram showing a functional block of the image acquisition operation management part 101 according to Embodiment 1. The image acquisition operation management part 101 is a functional block realizing the operation in the image acquisition operation (S104). It has an external device control interface part 1010 for instructing control to the devices such as the conveying mechanism control part 10 and the image reading unit control part 6 controlled by the system, an image acquisition parameter storing part 1013 for managing image acquisition time, a timer 1012 for monitoring time, a controlled variable obtaining part 1015 obtaining the controlled variable of the unit such as the conveying mechanism from the data processing part 102, a sequence operation order storing part 1014 storing the procedure of the conveying operation and the image acquisition sequence operation, and a sequence operation processing part 1011 sequentially sending an operation signal to the external devices according to the sequence operation procedure to execute the image acquisition operation.

FIG. 5B is a diagram showing an example of a data table 1016 stored in the sequence operation order storing part 1014 according to Embodiment 1. As shown in the table 1016, in the conveying and image acquisition operations necessary for image acquisition, the operation order of all the devices mounted on the system such as control of the driving part such as a motor provided in the conveying mechanism, the number of set growing cases, and photographing illumination control is sequentially stored. When the construction of the conveying mechanism or the number of growing cases is changed, the configuration having the storing part 1014 can change the sequence operation only by rewriting the contents of the storing part to easily change the system configuration.

Figure 6:
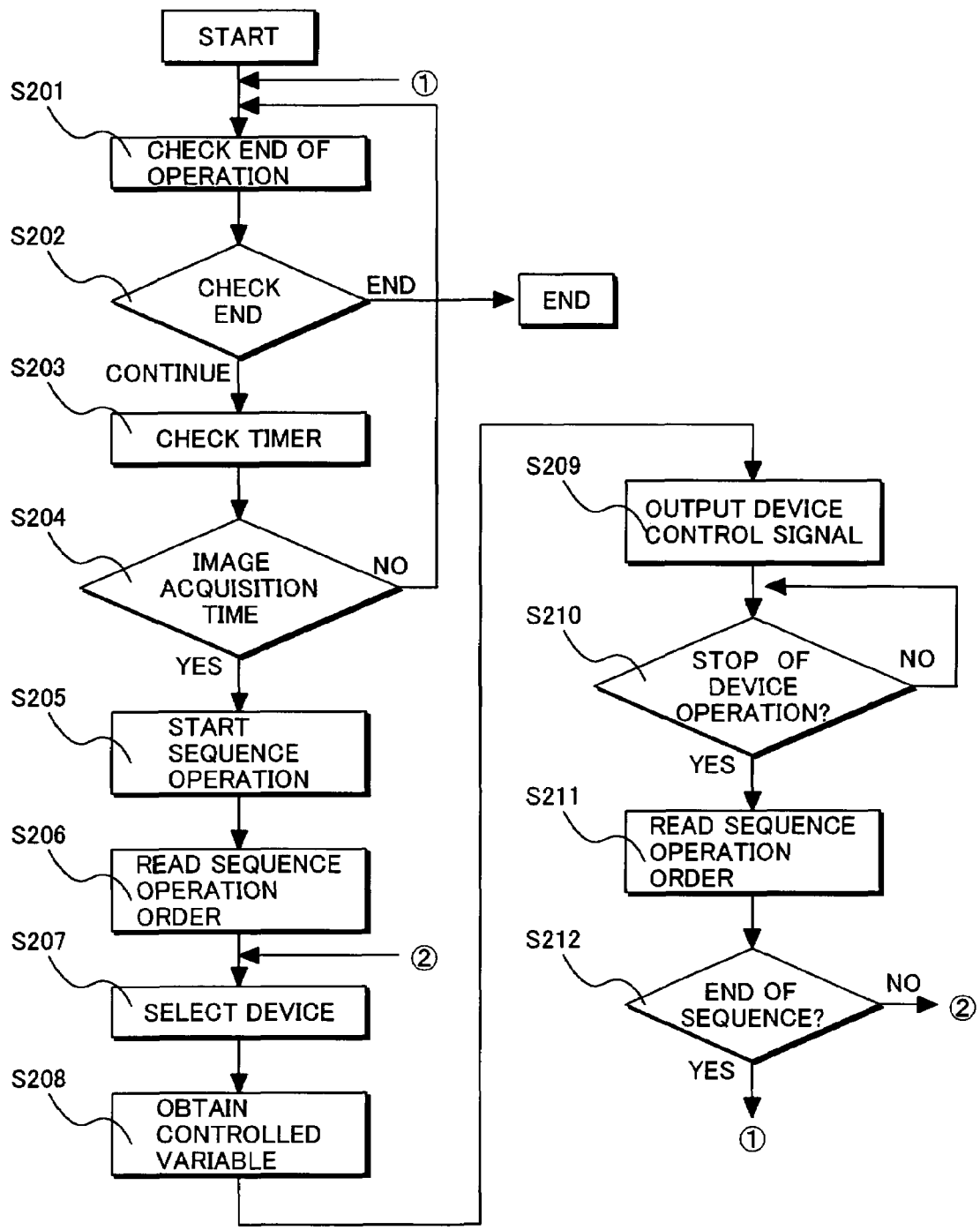
FIG. 6 is a diagram showing a processing operation flow of the image acquisition operation management part 101 according to Embodiment 1.

FIG. 6 is a diagram showing a processing operation flow of the image acquisition operation management part 101 according to Embodiment 1.

After starting the image acquisition operation, whether there is an instruction of end of the operation at the start of the photographing operation is checked (S201). When there is an instruction for ending (S202), the photographing operation is ended. The instruction for ending the operation is performed by sending a signal of the operation ending to the image acquisition operation management part 101 when the user performs the end operation (or depresses the experiment end button) on the console panel (see FIG. 4B). Time is checked (S203), and when it is image acquisition time (S204), the image acquisition sequence operation is started (S205). In the sequence operation, according to the sequence operation order storing part 1014, the sequence operation processing part sequentially performs operation instruction to the external devices. The sequence operation order is referred (S206) to select the control device for control (S207) for obtaining the controlled variable of the device from the controlled variable obtaining part 1015 (S208). The operation signal of the obtained controlled variable is outputted via the external device control interface 1010 to the target device (S209) to operate the device. After outputting the operation signal of the device, the completion of the operation of the device is waited for (S210), and then, the next sequence operation order is read (S211). When there is the next sequence operation, the operation is performed again (S27). When the sequence is ended, the next image acquisition operation time is waited for (S201).

Figure 7A:
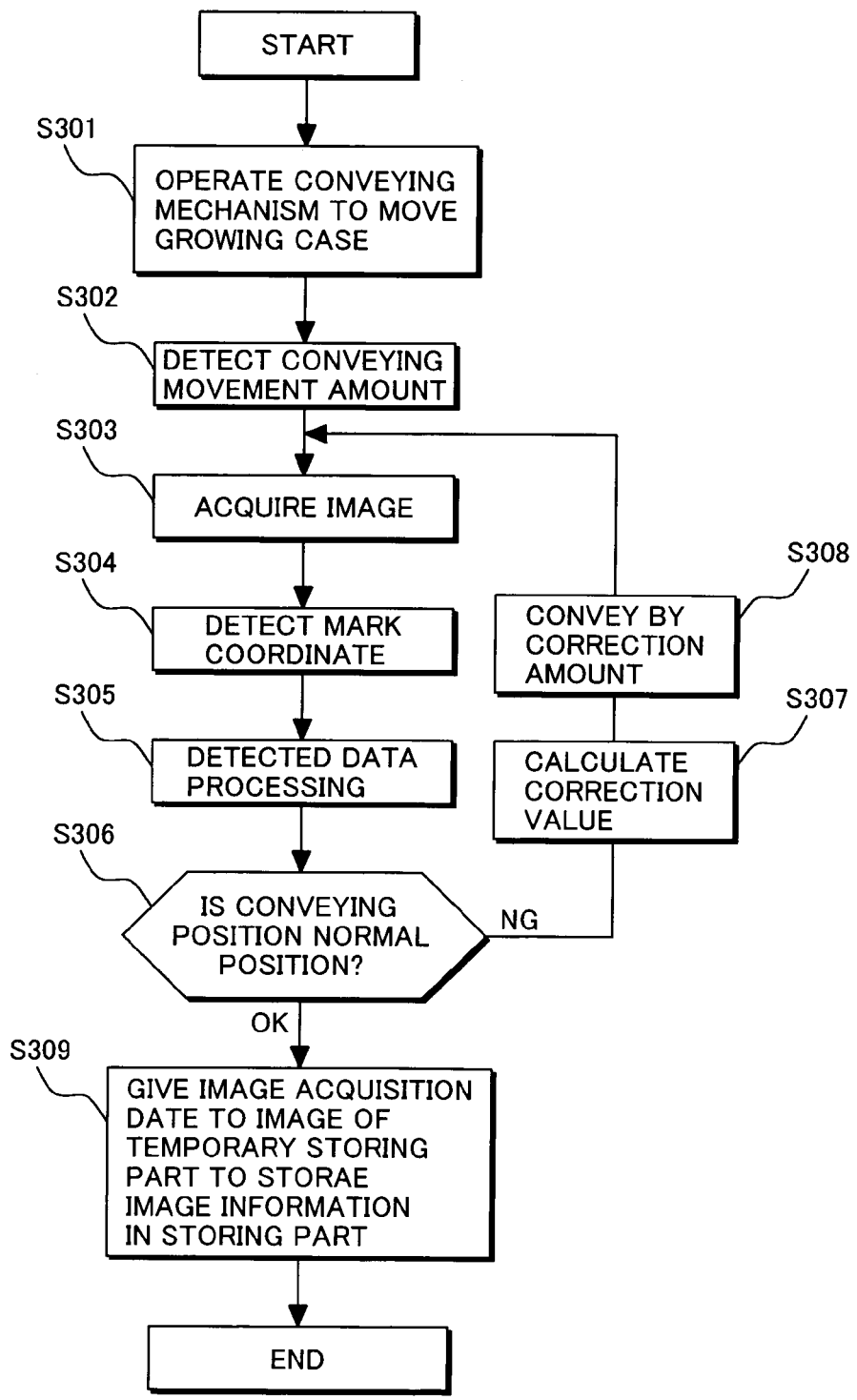
FIG. 7A is a diagram showing a processing flow of a photographing sequence operation according to Embodiment 1.
Figure 7B:
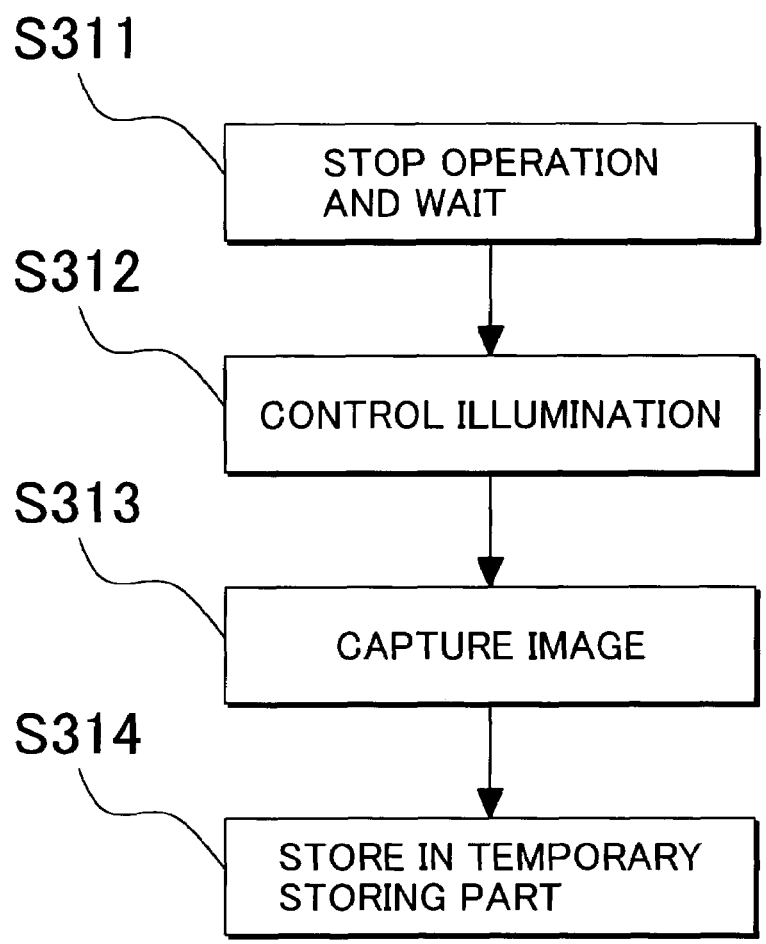
FIG. 7B is a diagram showing a processing flow of an image acquisition operation according to Embodiment 1.

FIGS. 7A and 7B are diagrams showing the detail of the correction processing operation and the photographing operation of the conveying control in the image acquisition operation according to Embodiment 1.

FIG. 7A is a diagram showing a processing flow of a photographing sequence operation according to Embodiment 1.

According to the stored contents of the sequence operation order storing part 1014, the conveying operation 9 is operated to move the growing case 13 to the image reading position of the camera 15 incorporating the image reading part 5 (S301). The conveying amount is obtained by the conveying movement amount detection part 11 (S302) to perform image acquisition (S303). The position detecting mark 14 added to the growing case 13 in the acquired image is detected by the image processing part 105 to specify the coordinate position of the mark 14 (S304). The detected coordinate position data is processed by the data processing part 102 (S305). The data processing part 102 determines whether the conveying position is the normal position (S306). When the determined result is NG, a deviation from the normal position is obtained to calculate a conveying amount correction value necessary for conveying to the normal position (S307) for operating the conveying mechanism 9 according to the calculated correction value to move the growing case 13 (S308). The operation is repeatedly performed until the conveying position is stopped in the normal position, and then, an image of the growing case 13 is acquired for each operation (S303).

After determining that the growing case 13 is conveyed to the normal position, information such as an image acquisition date is given to an image photographed immediately before being stored in the temporary storing part 104 to store it in the image information storing part 106 (S309). In such method, it is possible to acquire an image in which the physical position relation between the camera and the growing case by an operation error in the conveying operation which is a problem when using the conveying mechanism is maintained with high accuracy, thereby realizing measurement of the growing process with high accuracy.

FIG. 7B is a diagram showing a processing flow of an image acquisition operation according to Embodiment 1.

In the image acquisition operation, there is a phenomenon in which the growing case 13 is vibrated after conveying. About a few seconds are waited for after conveying (S311). Based on the photographing parameter, control of turning on and off illumination is performed (S312) to capture an image (S313). The read image data is transferred to and stored in the temporary storing part 104 (S314).

Figure 8:
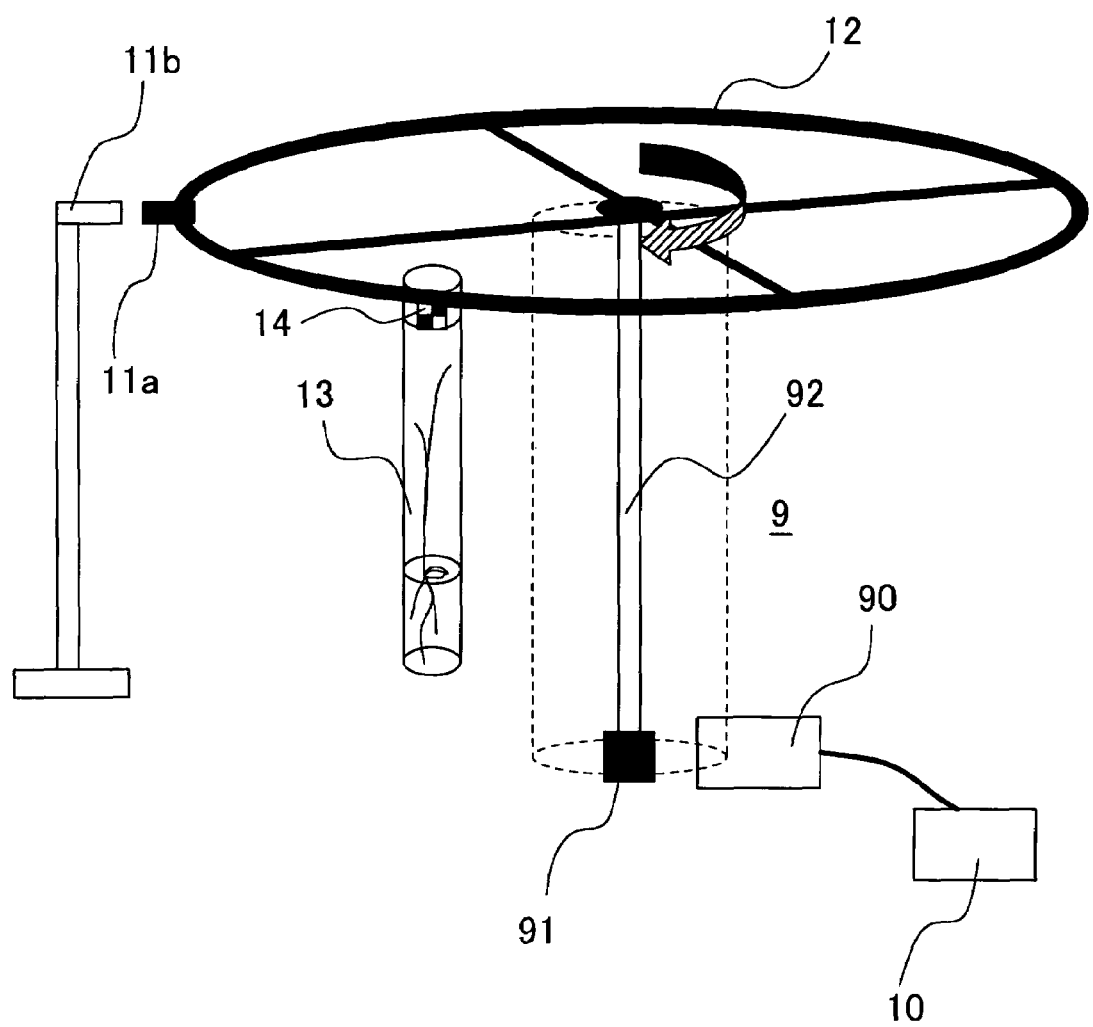
FIG. 8 is a diagram showing the constructions of a conveying mechanism 9 and a conveying mechanism operation amount detection part 11 according to Embodiment 1.

FIG. 8 is a diagram showing the constructions of the conveying mechanism 9 and the conveying mechanism operation amount detection part 11 according to Embodiment 1.

In Embodiment 1, the conveying mechanism 9 has means setting a plurality of the growing cases 13 on a ring-like table 12 rotatably operated in the arrow direction shown in the drawing. The ring-like table 12 conveying the growing cases 13 is rotatably operated by a pulse motor 90, a gear box 91 and a rotating axis 92. The rotating operation can be controlled-by the number of revolutions of the pulse motor 90 operated in response to a pulse signal given from the conveying mechanism control part 10. This construction can easily correspond the controlled variable of the motor with the rotation angle of the table, facilitating the control. A direct drive motor can be used instead of the pulse motor 90. In this case, the table can be directly conveyed and the gear box 91 is unnecessary. In this case, like the pulse motor, the conveying control can be performed by the number of revolutions of the motor.

To detect the movement amount of the table 12 of the conveying mechanism 9, a detection section 11a for detecting the rotation amount and a position detection sensor 11b corresponding to this are provided in the end surface position of the table 12. Although only one detection section 11a is shown in the drawing, many detection sections 11a are provided at equal intervals to enhance the resolution of the detection of the rotation amount of the table 12. The position detection sensor 11b gives a pulse output corresponding to the passage of the detection section 11a. When measuring the pulse output, the rotation amount of the table 12 can be easily detected. The detecting mark 14 for detecting the position movement amount from the acquired image is attached to the growing case 13. Although the detecting marks 14 are attached to the upper and lower sides of the growing case 13 in FIG. 3, one detecting mark 14 may be attached thereto. Data of the operation movement amount obtained from the position detection sensor 11b or the image is sent to the data processing part 102 to be used for the rotation control of the table 12 and the correction control of the conveying amount. It is also effective, when the operation is abnormal, for specifying whether it is caused by the motor or table.

Figure 9A:
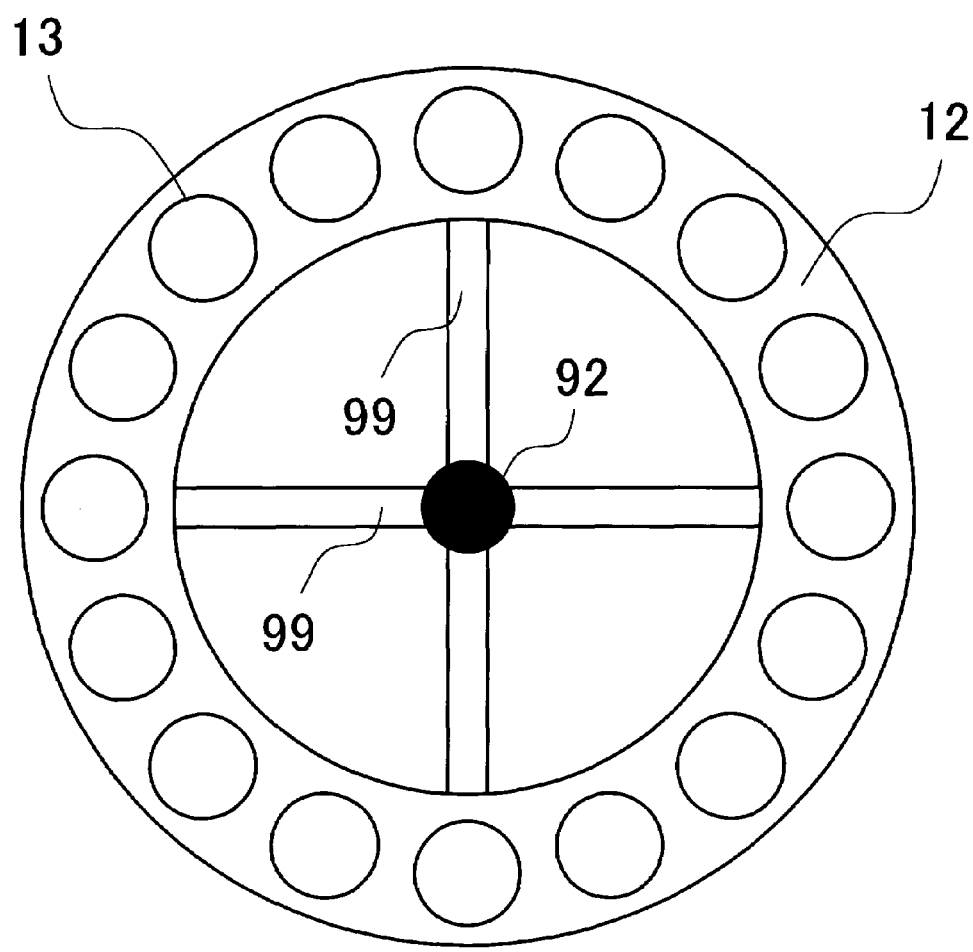
FIG. 9A is a diagram of a ring table 12 fixing growing cases 13 according to Embodiment 1 viewed from the top.
Figure 9B:
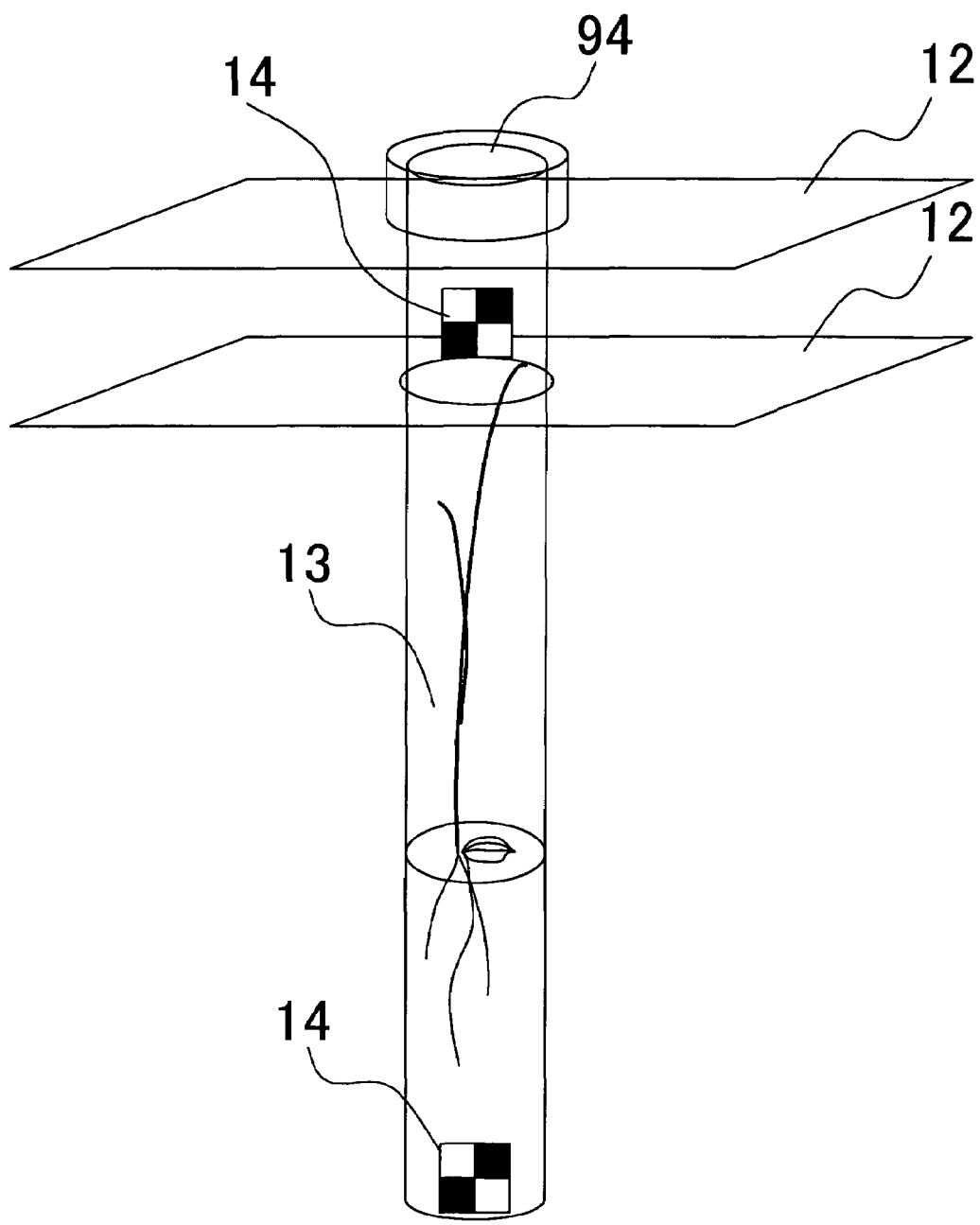
FIG. 9B is a diagram by taking out the relation between the ring tables 12 and the growing case 13 according to Embodiment 1.
Figure 9C:
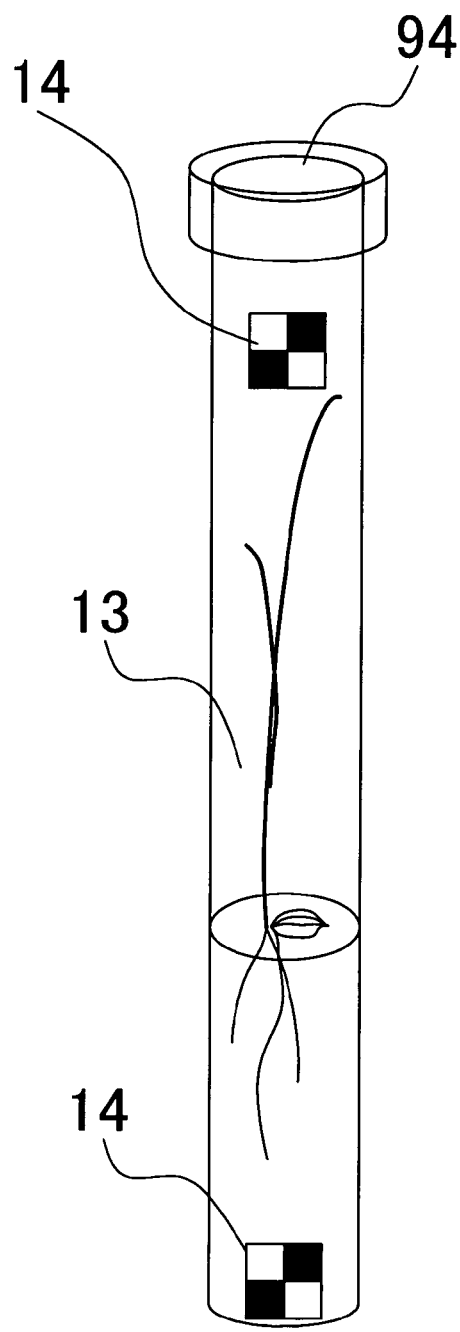
FIG. 9C is a diagram by taking out the growing case 13 and position detecting marks 14 according to Embodiment 1.

FIGS. 9A to 9C are diagrams showing an example of a method of fixing the growing cases 13 and a method of attaching the position detecting marks 14 according to Embodiment 1.

FIG. 9A is a diagram of the ring table 12 fixing the growing cases 13 according to Embodiment 1 viewed from the top. The table 12 fixing the growing cases 13 is a circular ring table made of a thick material. Holes through which the main bodies of the growing cases 13 can be inserted are opened in the circumferential portion of the ring table 12 and the growing cases 13 are inserted downwardly into the holes. A holding part 94 larger than the main body of the growing case 13 is formed in the upper end portion of the growing case 13 and cannot be passed through the hole through which the main body of the growing case 13 can be inserted. The growing case 13 is held on the ring table 12. Beams 99 crossing the center portion of the ring table 12 are provided to be fixed onto a driving shaft 92 for rotating the table in the cross portion. The rotation motion of the conveying motor rotates the table 12 via the shaft 92.

FIG. 9B is a diagram by taking out the relation between the ring tables 12 and the growing case 13 according to Embodiment 1. In this example, there are two ring tables 12. The holding part 94 of the growing case 13 is larger than the main body of the growing case 13. The growing case 13 is held to be hung down from the ring table 12. In this case, although not shown in the drawing, the hole of the ring table 12 in the upper stage may be engaged with the holding part 94 so that no relative rotation of the growing case 13 with the ring table 12 occurs. The table 12, which is ring like, is desirably made of a material not interrupting light which is important for growing a plant, e.g., a material such as acryl. When the table is a plate, the material not interrupting light is essential. The two tables 12 can prevent the growing case 13 from being vibrated during the conveying operation and from being rotated or vibrated right and left.

FIG. 9C is a diagram by taking out the growing case 13 and the position detecting marks 14 according to Embodiment 1. The position detecting marks 14 may be attached to the upper and lower sides of the growing case 13. The design of the mark 14 which facilitates position detection image processing is effective. This embodiment uses the mark of design as shown in FIG. 9C. Attaching at least one mark for detecting the position of the growing case 13 permits detection. As shown in the drawing, two position detecting marks 14 are attached to two positions in the upper and lower directions or more of the growing case 13 so as to detect an error of the positions in the right and left directions and in the rotation direction, thereby increasing the detection accuracy of the error of the conveying position. The mark 14 may be attached directly to the conveying mechanism on the outer circumference surface of the table 12 other than the growing case 13 depending on the configuration of the system.

Figure 10A:
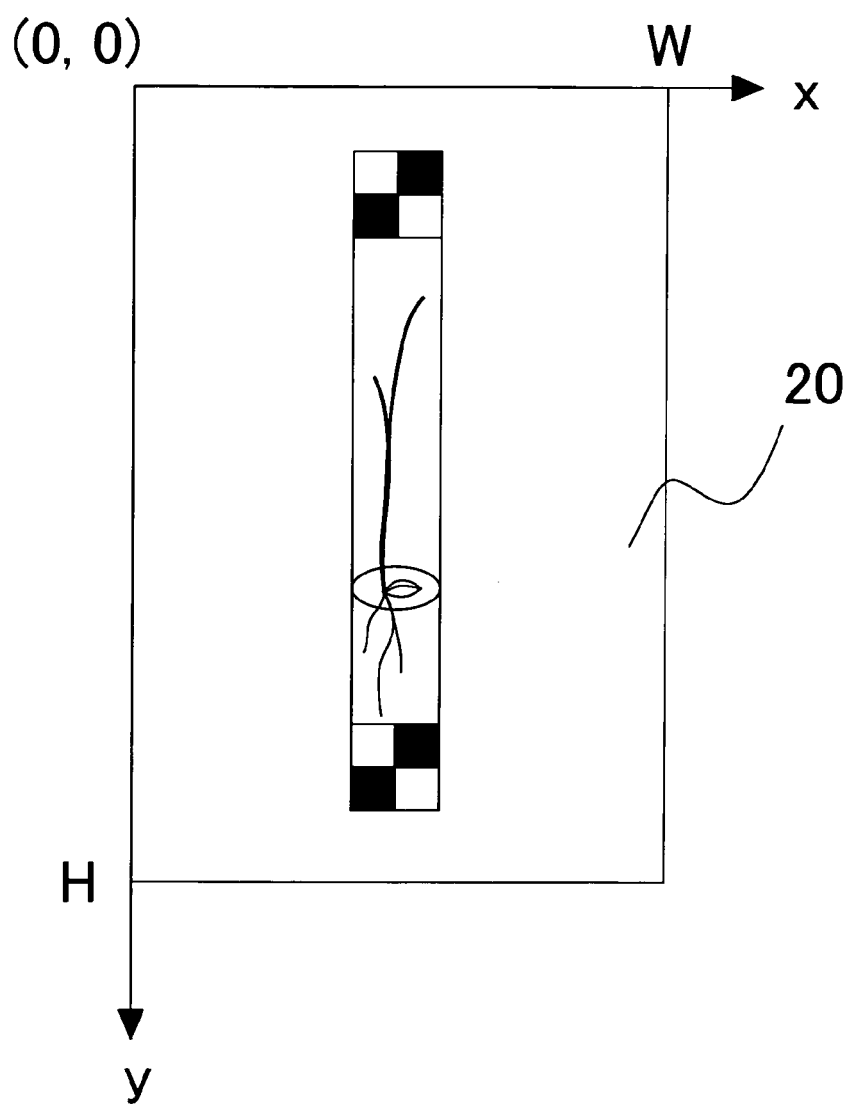
FIG. 10A is a diagram showing an example of an image of the growing case 13 acquired in the state of attaching the position detecting marks 14 according to Embodiment 1.
Figure 10B:
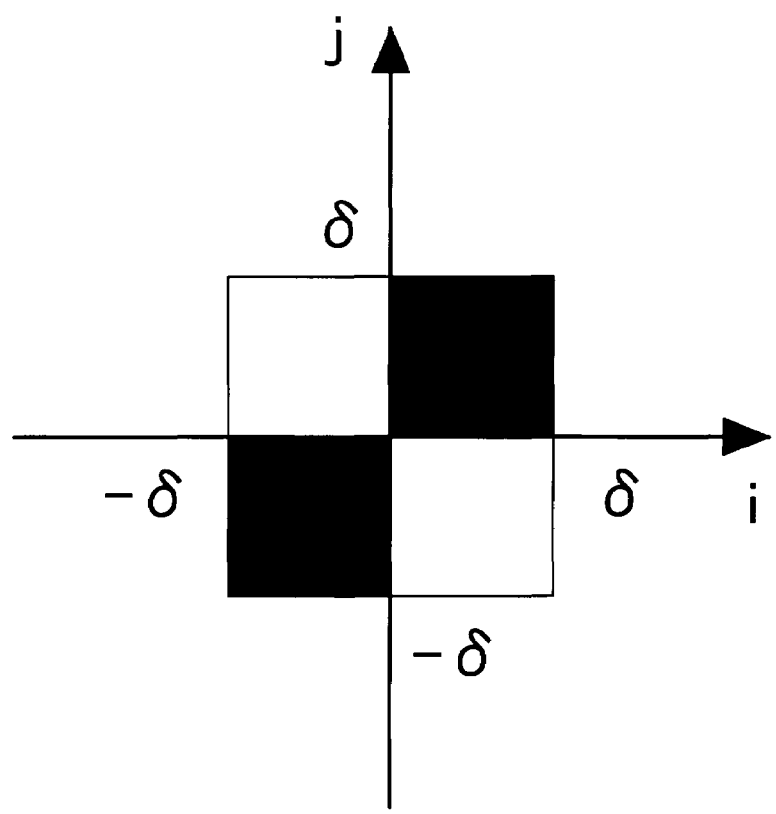
FIG. 10B is a diagram showing an image prepared as a template image according to Embodiment 1.
Figure 10C:
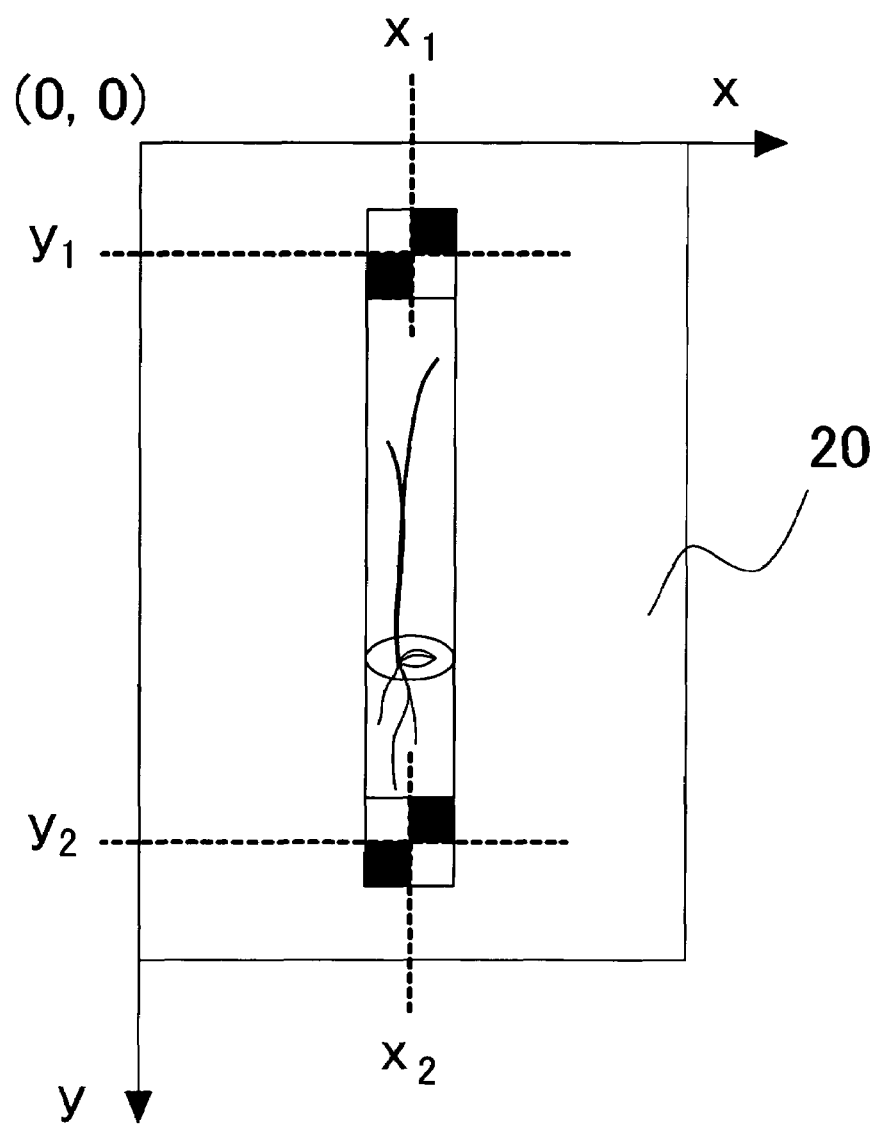
FIG. 10C is a diagram showing a detected result example of the position detecting marks 14 according to Embodiment 1.

FIGS. 10A to 10C are diagrams of assistance in explaining a position detection method using the position detecting marks according to Embodiment 1.

FIG. 10A shows an example of an image of the growing case 13 acquired in the state of attaching the position detecting marks 14 according to Embodiment 1. The image defines the coordinate of the image with the upper left side as an origin point. FIG. 10B is a diagram showing an image prepared as a template image according to Embodiment 1 and shows an image having the same design as that of the detecting marks 14. The image size is prepared to be matched with the detecting marks 14 in the acquired image. The acquired image and the template image are used to detect the position of the template image in the acquired image. In the detection process, a template matching method generally used in image processing is effective. The template matching calculates the values of Equation (1) for all the coordinates in the acquired image to output the coordinate (x, y) of the largest value as the detected result.

$$h(x, y) = \sum_{j=-\delta}^{j=\delta} \sum_{i=-\delta}^{i=\delta} \|f(x+i, y+j) - t(i, j)\| \quad (1)$$

$$(\delta < x < W - \delta, \delta < y < H - \delta)$$

where h (x, y): an evaluation coefficient for mark detection, x, y: coordinate values in an image for mark detection, i, j: coordinate values in a template image, δ (delta): a value determined by template image size, W: the width of an image for mark detection, and H: the height of an image for mark detection.

FIG. 10C is a diagram showing a detected result example of the position detecting marks 14 according to Embodiment 1. In this case, two marks exist and the two higher-order evaluation coefficients obtained by Equation (1) are calculated as detected results.

Figure 11:
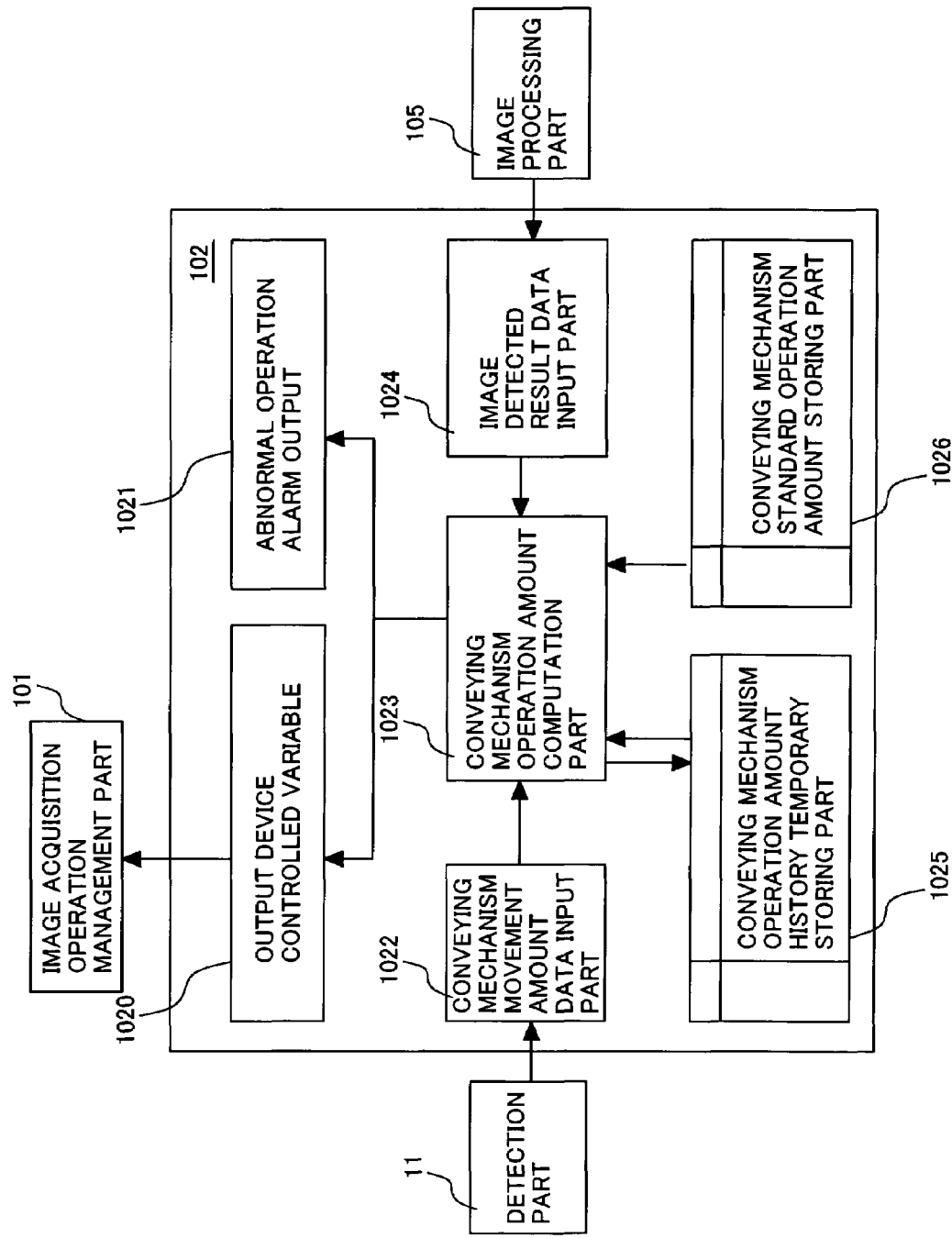
FIG. 11 is a diagram showing a functional block of a data processing part 102 according to Embodiment 1.

FIG. 11 is a diagram showing a functional block of the data processing part 102 according to Embodiment 1.

Data of the mechanism movement amount detected by the conveying mechanism movement amount detection part 11 is inputted via a mechanism movement amount data input part 1022 to a conveying mechanism operation amount computation part 1023. The mark position coordinate data detected by the image processing part 105 is inputted via an image detected result data input part 1024 to the conveying mechanism operation amount computation part 1023 and is stored in a conveying mechanism operation amount history temporary storing part 1025. The standard operation data amount of the conveying mechanism is stored in a conveying mechanism standard operation amount storing part 1026. After the conveying operation, based on the mechanism movement amount data and the image detected result detected by the conveying mechanism movement amount detection part 11, the correction value of the operation amount necessary for stopping in the correct conveying position is calculated by the conveying mechanism operation amount computation part 1023. The difference between the calculated result and the standard operation data of the conveying mechanism is corrected to be outputted via a device control amount output 1020 to the image acquisition operation management part 101. When the result obtained by computing the conveying operation amount from the data inputted from the data input parts 1022 and 1024 is an infinite value in which the conveying operation is impossible, the abnormal conveying operation is determined to perform display or give an alarm that an abnormal condition occurs via an abnormal operation alarm output 1021 or on the display device 4. At this time, of course, the operation is locked.

Figures 12A, 12B:
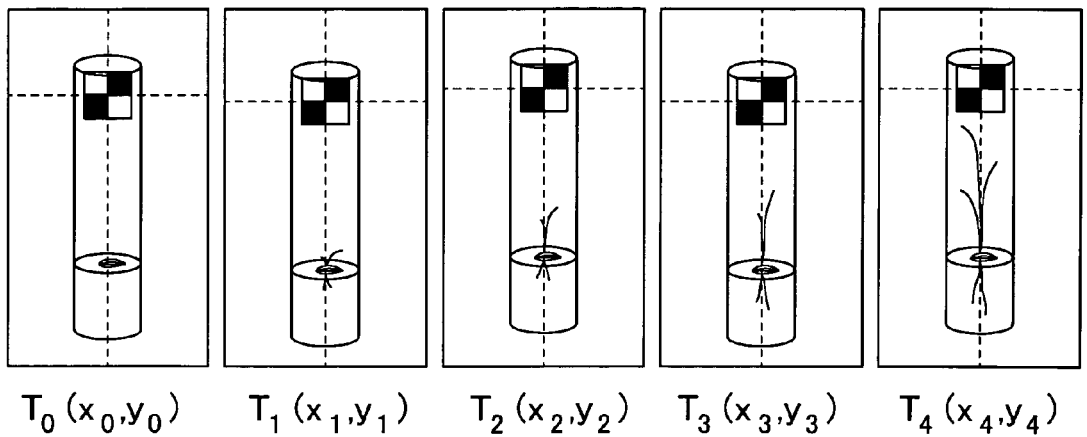
FIG. 12A is a diagram showing an example of a device movement amount data table obtained from the conveying mechanism movement amount detection part 11 according to Embodiment 1.
FIG. 12B is a diagram showing the center coordinates of detected marks.
Figures 12C, 13A:
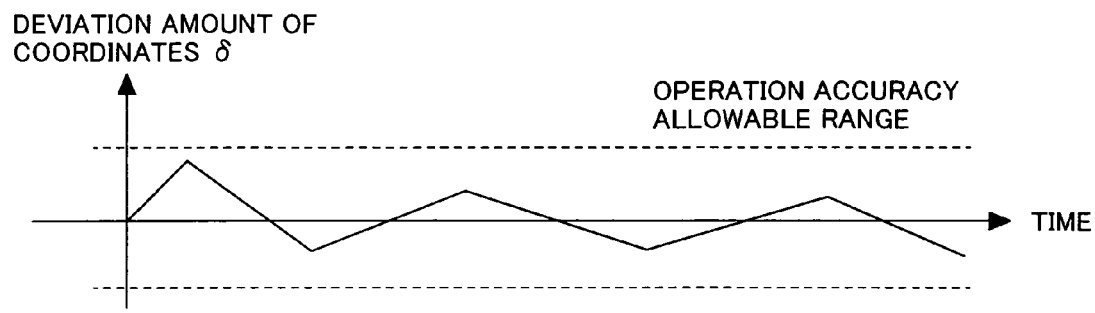
FIG. 12C is a diagram showing a chronological deviation amount of the detected coordinates.
FIG. 13A is a diagram showing an example of a data table of a conveying mechanism operation history temporary storing part 1025 according to Embodiment 1.

FIGS. 12A to 12C are diagrams showing an example of data detected from the detection part and the image processing part according to Embodiment 1.

FIG. 12A is a diagram showing an example of a device movement amount data table obtained from the conveying mechanism movement amount detection part 11 according to Embodiment 1. As shown in FIG. 12A, data of an actual operation date, an instruction value of the motor instructed in operation, and a table movement amount in which the table is actually moved are stored. The storing matching the conveying instruction amount transmitted from the device control amount output 1020 with the actual conveying amount is utilized and can be utilized as information when calculating the correction value of the conveying amount and specifying the cause at trouble in which the conveying cannot work well.

FIG. 12B is a diagram showing the center coordinates of detected marks. The coordinate values indicate coordinate values in the coordinate system with the upper left side of an image as an origin point.

FIG. 12C is a diagram showing a chronological deviation amount of the detected coordinates. Based on the coordinate values shown in FIG. 12B, a deviation amount is obtained by Equation (2)

$$\delta_i = \sqrt{(y_i - y_0)^2 + (x_i - x_0)^2} \ (i=0,1,\ldots) \quad (2)$$

where i: the total number of times of image acquisition of a target image, δi (delta): a deviation amount of the ith image, xi, yi: coordinate values in a target image, and x0, y0: coordinate values of the mark detected result of an image of i=0.

Consequently, the chronological change of image shift due to the operation error of the conveying mechanism is obtained as the result of the graph shown in FIG. 12C. Whether it is within the allowable range of the operation accuracy of the conveying mechanism can be determined.

As described above, the operation state is stored to serve as detection of an abnormal condition of the system and calculation of an optimum correction value.

FIGS. 13A and 13B are diagrams showing an example of temporarily stored data of the data processing part 102 according to Embodiment 1.

FIG. 13A is a diagram showing an example of a data table of the conveying mechanism operation history temporary storing part 1025 according to Embodiment 1. The data is a table storing data explained in FIGS. 12A and 12B in the chronological order. Data in one conveying operation, that is, all of a motor operation amount, a table movement amount and a mark position detected after operation.

FIG. 13B is a diagram showing an example of a data table of the conveying mechanism standard operation amount storing part 1026 according to Embodiment 1. For data stored here, ideal values of a controlled variable of the conveying mechanism of the system and detected data after conveying for all the conveying operations of the system are stored. With reference to the data, conveying control is performed. The data is determined in each system and must be stored before starting the operation of the system. Only the value of the conveying operation amount of the storing part as a standard value is controlled to compare detected data after operation with the value of the storing part. When the values are different, the difference indicates a conveying error.

Matching of the deviation amount with the conveying amount appearing as an error of a mark detection position is determined by matching with the operation amount of the driving part used in the system. The matching can be obtained by performing a test operation (a motor operation amount, a movement amount and an image mark detection operation) in the design of the conveying mechanism and completing the system.

FIGS. 14A and 14B are diagrams showing an example of a data table of stored data of the image information storing part 106 and the analyzed result storing part 3 according to Embodiment 1.

FIG. 14A is a diagram showing an example of data of the image information storing part 106 according to Embodiment 1. As shown in the table, a serial number (sample No.) is given to each of the growing cases for management for each sample No. An image acquisition date and the environmental conditions (such as temperature and humidity) are stored in each acquired image, which is effective for growing analyzing information.

FIG. 14B is a diagram showing an example of data of the analyzed result storing part 3 according to Embodiment 1. As shown in the table, data is obtained by adding analyzed data (the length and angle of the leaves and root of an object) obtained from image information stored in FIG. 14A. The growing image and the analyzed data are managed together so that the numerical value data of growing can be evaluated while viewing an image, thereby efficiently performing an analyzing work.

Figure 15A:
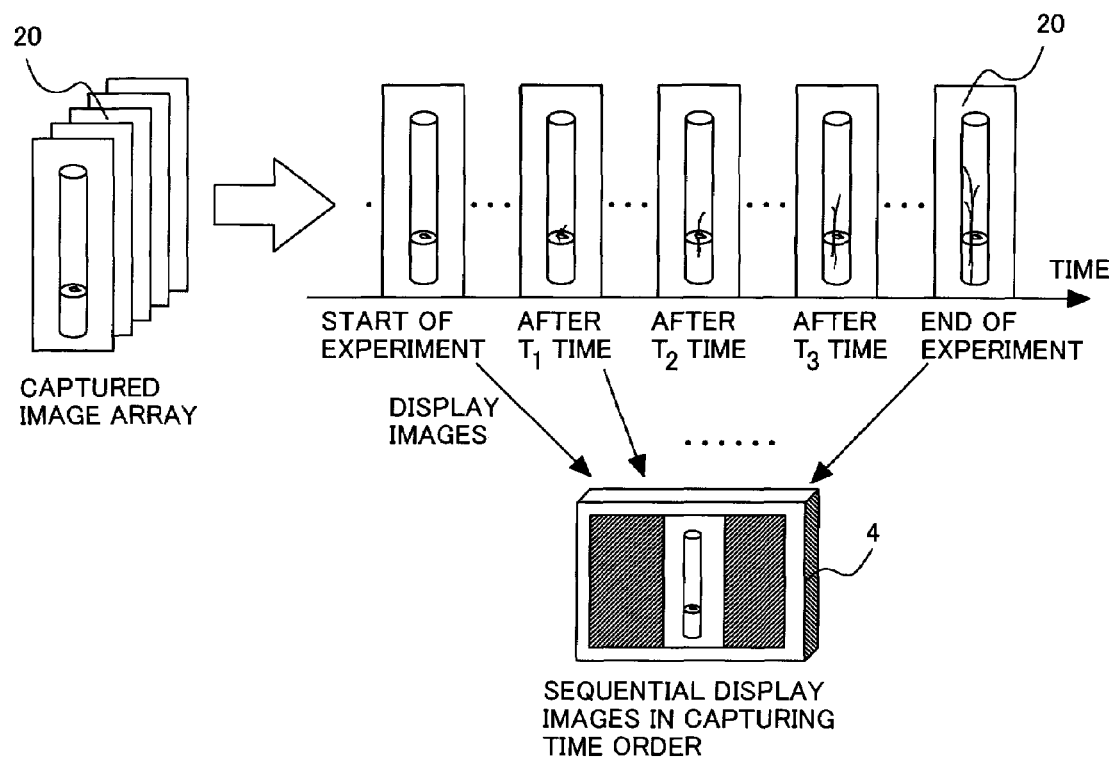
FIG. 15A is a diagram showing an analyzing processing flow of pseudo moving image display using an acquired image array according to Embodiment 1.
Figure 15B:
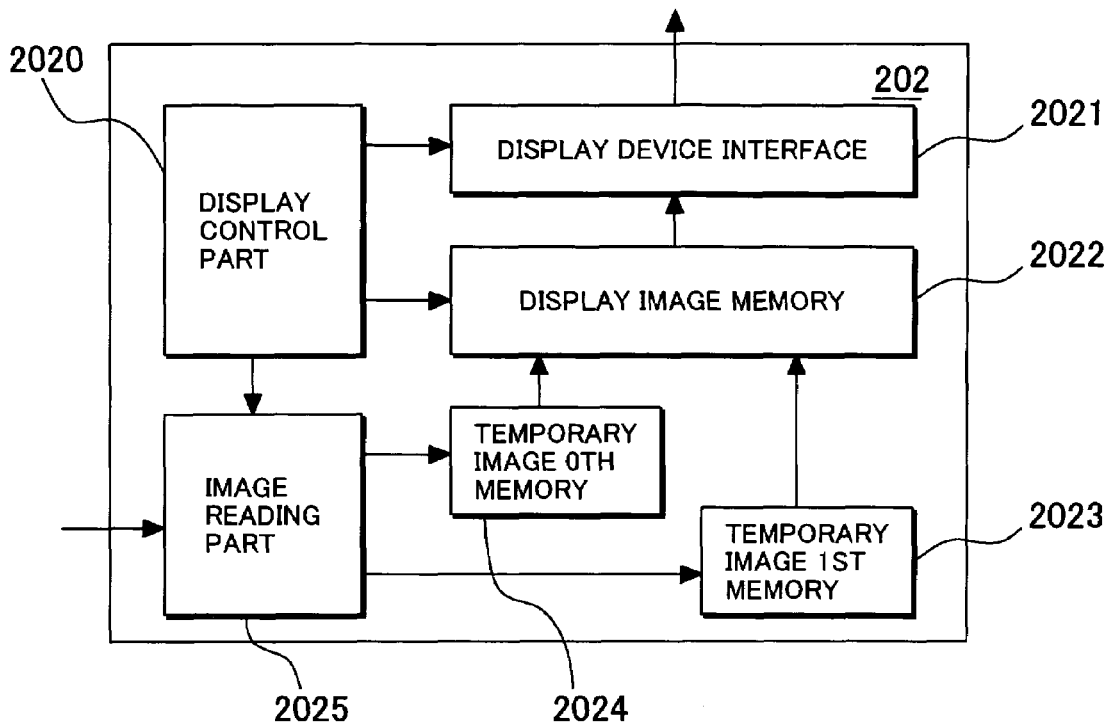
FIG. 15B is a diagram showing a functional block of a display control part 202 realizing performing pseudo moving image display according to Embodiment 1.

FIGS. 15A and 15B are diagrams showing an example of a process in an image analyzing processing part 201 in the image analyzing part 2 according to Embodiment 1 and a functional block of an image display control part 202 which has received the output of the image analyzing processing part 201.

FIG. 15A is a diagram showing an analyzing process flow of pseudo moving image display using an captured image array according to Embodiment 1. As shown in the drawing, the pseudo moving image display is processing for chronologically arranging captured images 20 to sequentially display them on the display device. The captured images are moving image displayed to display slow changes in a plant as changes in the changing speed which can be identified by a human, thereby obtaining the effect for change analyzing. FIG. 15B is a diagram showing a functional block of the display control part 202 realizing performing pseudo moving image display according to Embodiment 1. The acquired images are sequentially read by an image reading part 2025 to alternately develop image data in a temporary storing 0th memory 2024 and a temporary storing 1st memory 2023. The developed image data are alternately transferred to a display image memory 2022 and are displayed via a display device interface 2021 on the display device 4. The two temporary image memories are used to permit flicker-free display. A series of the processing is performed by a display control part 2020.

Figure 16A:
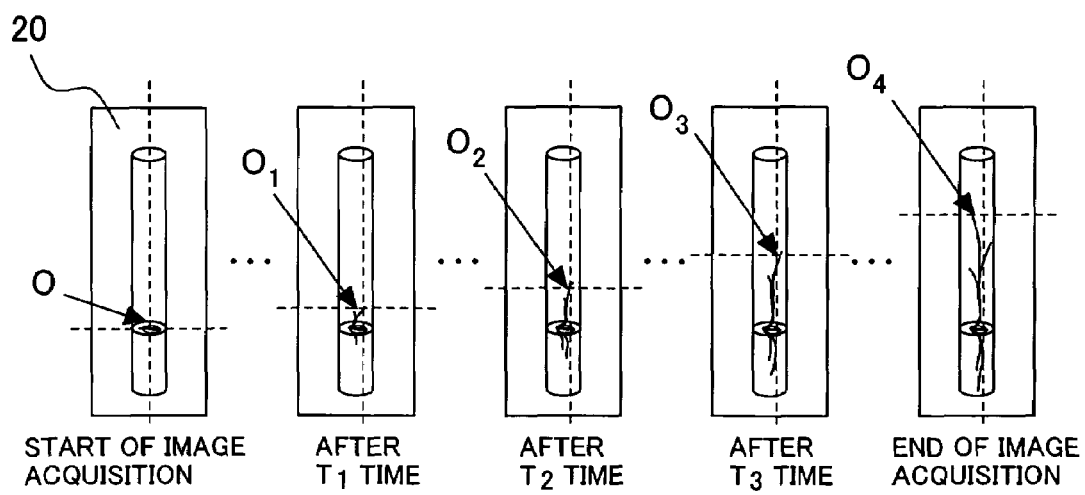
FIG. 16A is a diagram showing a flow of detection of the edge part of a plant according to Embodiment 1.
Figure 16B:
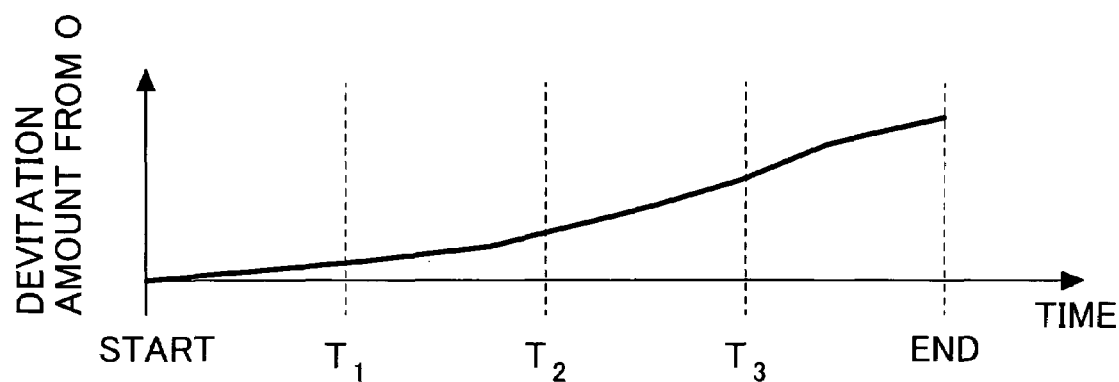
FIG. 16B is a diagram showing graph display of a detected result of the growing edge part of a plant in the processing of FIG. 16A.
Figure 16C:
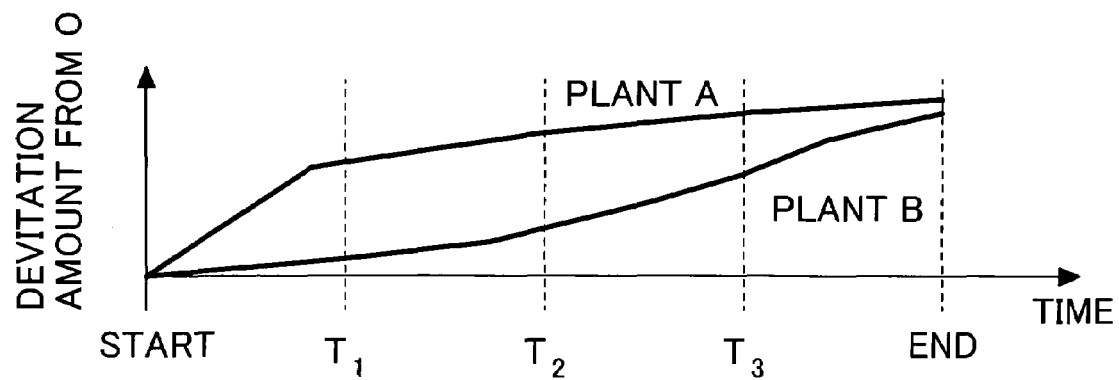
FIG. 16C is a diagram showing an example in which the growing speeds of the growing edge parts of plants are compared.

FIGS. 16A to 16C are diagrams of assistance in explaining growing speed measurement of the image analyzing processing part 201 according to Embodiment 1. As another example of the analyzing method using an acquired image line, an example of growing speed measurement by detecting the edge part is shown.

FIG. 16A is a diagram showing a flow of detection of the edge part of a plant according to Embodiment 1. As shown in the drawing, the growing edge part of a plant for all images acquired from the start of image acquisition is detected. The deviation amount from the start of an experiment at the coordinates of the acquired edge part is calculated by the same computation equation as Equation (2).

FIG. 16B is a diagram showing graph display of a detected result of the growing edge part of a plant by the processing of FIG. 16A. Small changes in the shape of growing difficult to evaluate only by eyes are expressed as successive numerical value data. Changes in the shape of a growing process can be quantitatively evaluated and the difference in growing between many plants can be quantitatively compared.

FIG. 16C is a diagram showing an example in which the growing speeds of the growing edge parts of plants are compared. The graph shows an example in which the measured result shown in FIG. 16B for two plants are analyzed. As in this example, it is possible to read that plants A and B in which final lengths are almost matched are plants having different changes in their growing process. Such results can be obtained from image acquisition of a plurality of plants and the analyzed results.

Figure 17:
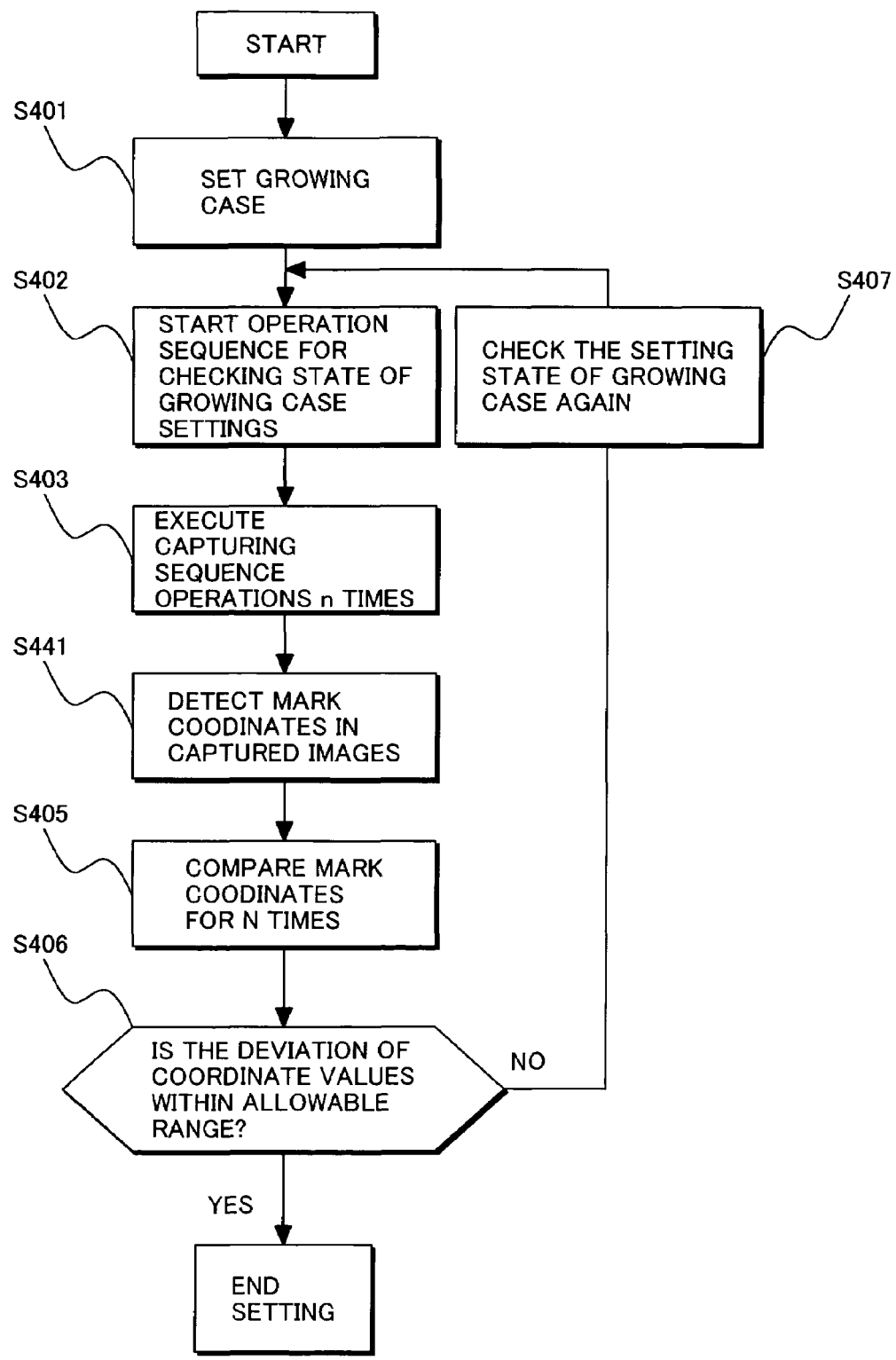
FIG. 17 is a diagram showing an automatic check function processing flow of the set growing case as an application operation of the system according to the present invention.

FIG. 17 is a diagram showing an automatic check function processing flow of the set growing case as an application operation of the system of the-present invention.

Fixedly setting of the growing case 13 on the conveying mechanism 9 is important for maintaining the physical position accuracy of the camera 15 and an observed plant. It is desirable to check at setting whether the growing case 13 is fixedly set on the conveying mechanism 9 and to check that it is fixed on it. Check operation processing for that is proposed. A growing case is set (S401) to execute a setting check operation sequence (S402). In the operation, desirably, the operation speed is increased than normal, operation and stopping are repeated, and intentional vibration is performed.

After performing such operation, normal photographing operations are executed n times (n>1) (S403). The mark coordinates in the photographed images for n times are detected (S404) to obtain the deviation of the coordinates (S405). Whether the obtained deviation is within in the allowable range of the photographing operation is determined (S405). Setting of the allowable range is determined corresponding to the measurement accuracy of target analyzing. As a result, when the determined result is failed, the setting state is checked again, which is repeated until the determined result is passed. As described above, the acquired image is used to check the setting state, thereby checking all the operation error factors.

Embodiment 2

There has been described the embodiment using small plants grown in test tubes. Actually, there are large plants grown to be above 1 m. The present invention can be applied to an analyzing system for such plants. When a plant is large, the amount of change in the shape of growing is large. To acquire growing images of many samples, securing a growing space is a problem.

Figure 18:
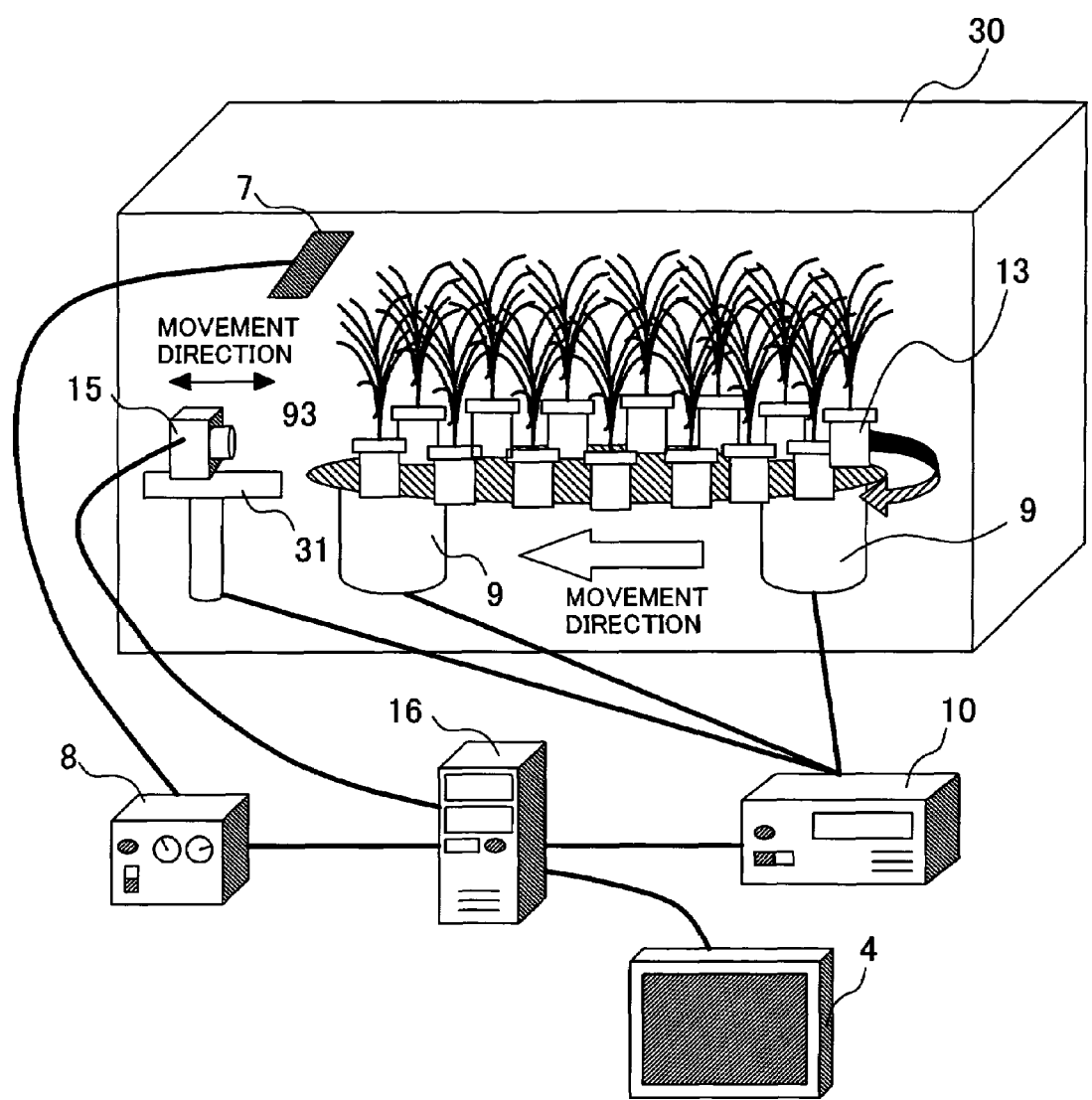
FIG. 18 is a schematic diagram of a system according to Embodiment 2 applying the system according to the present invention to large plants.

FIG. 18 is a schematic diagram of a system according to Embodiment 2 applying the system of the present invention is applied to large plants. The same components as FIG. 3 showing the schematic diagram of the system of Embodiment 2 are indicated by similar reference numerals. As is apparent by comparison of FIG. 18 with FIG. 3, also in Embodiment 2, the conveying mechanism 9 conveys the growing case 13 in the conveying direction, as indicated by the arrow, to perform image acquisition before the camera 15. The numeral 30 denotes a plant growing room.

In FIG. 18, since the growing cases 13 and the plants are large and heavy, the growing cases 13 are placed and conveyed on a table 93 mounted on the two interlocking conveying mechanisms 9. The camera 15 can be moved forward and rearward on a stage 31 to the table 93. This construction can be realized as in a movable stage used in an optical instrument.

The conveying control of the growing cases 13 in the construction of FIG. 18 is the same as the conveying mechanism of the growing cases 13 according to Embodiment 1 and can be embodied. The control to which the conveying mechanism of the camera 15 on the stage 31 is added can be realized by adding and storing data about the conveying of the camera 15 to data of the sequence operation order storing part 1014 explained in FIG. 5A and the conveying mechanism standard operation amount storing part 1026 explained in FIG. 11. The conveying mechanism is mounted on such image acquisition system to perform control of setting the image acquisition range at image acquisition by the stage 31 for each image acquisition. Depending on the size of the target growing case or the size of the target living body of image acquisition, image acquisition is permitted in an individually optimum position to increase the analysis accuracy. The entire system configuration of Embodiment 2 may be that shown in FIG. 1.

Embodiment 3

Figure 19A:
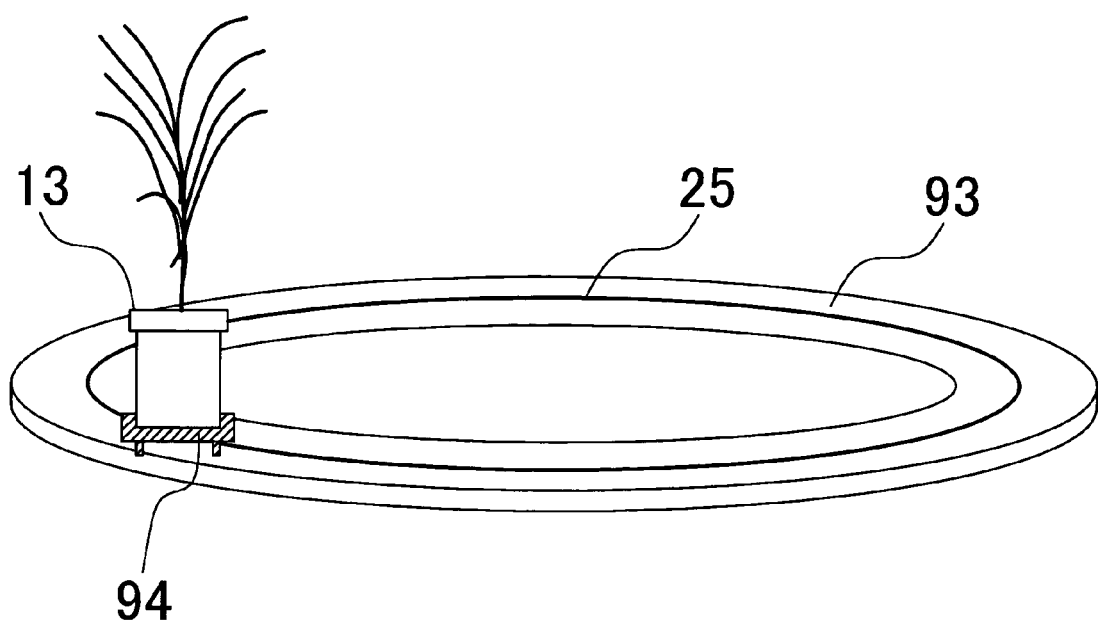
FIG. 19A is a diagram showing the conveying mechanism according to Embodiment 3 noting the growing case 13, growing case fixing means 94 and a table 93.
Figure 19B:
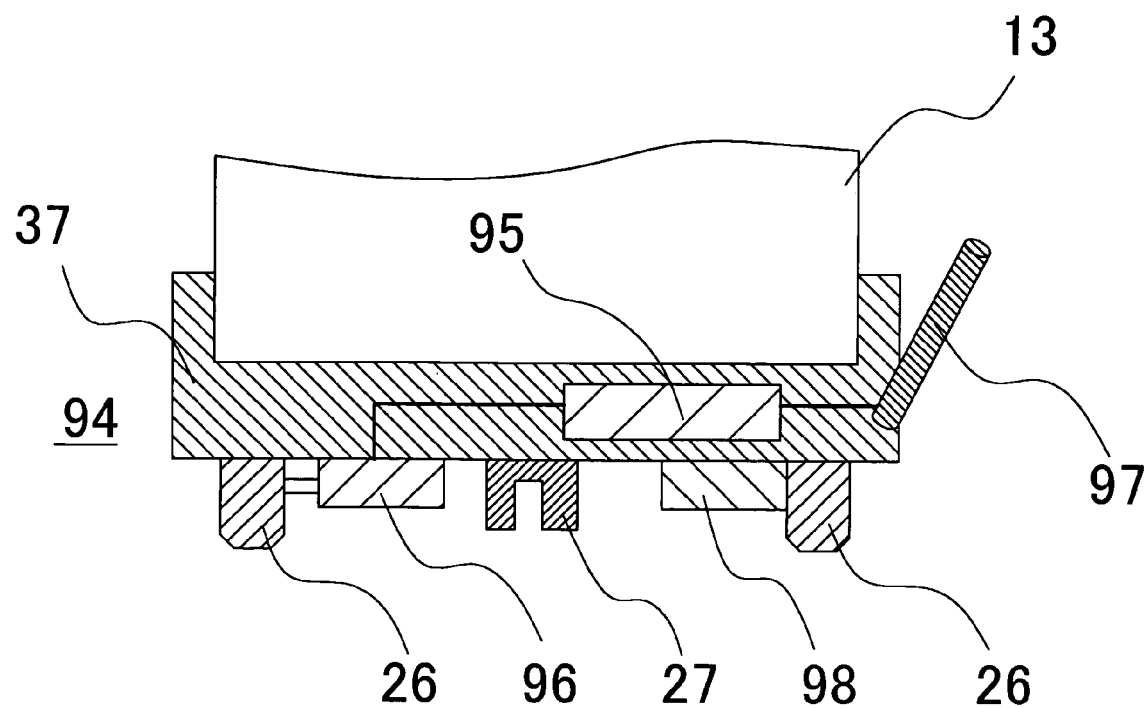
FIG. 19B is a diagram showing the detail of an example of the growing case fixing means 94 according to Embodiment 3.
Figure 19C:
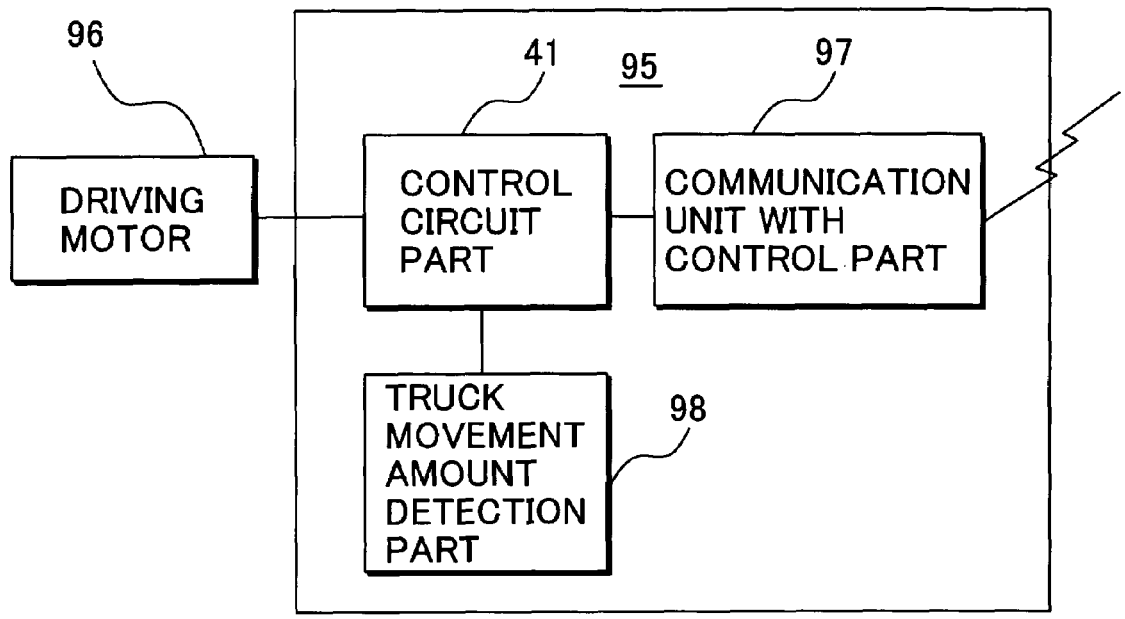
FIG. 19C is a diagram showing the detail of an example of a truck movement control part 95 according to Embodiment 3.

FIGS. 19A to 19C are diagrams of assistance in explaining Embodiment 3 which has basically a construction similar to that of as Embodiment 2 shown in FIG. 18, does not move the table 93 on which the growing case 13 is placed, and has a driving part for automating growing case fixing means 94 holding the growing case 13.

FIG. 19A is a diagram showing the conveying mechanism according to Embodiment 3 noting the growing case 13, the growing case fixing means 94 and the table 93. The numeral 25 denotes a monorail which is laid in the center portion on the surface of the table 93. The growing case fixing means 94 is guided by the monorail 25 in the state that the growing case 13 is placed to hold a fixed posture for being automated by the power of the driving part to convey the growing case 13.

FIG. 19B is a diagram showing the detail of an example of the growing case fixing means 94 according to Embodiment 3. The growing case fixing means 94 has a truck 37. The truck 37 has rising portions of its perimeter so that when the growing case 13 is placed on its top surface, the relation position with the truck 37 is in a predetermined state, and fixedly holds the growing case 13 thereby. The truck 37 has on its lower surface driving wheels 26 for automation and a guide 27 for being engaged with the monorail 25. It further has a driving motor 96 for rotating one of the driving wheels 26. As explained in Embodiment 1, the motor 96 can desirably control the conveying amount as one which can instruct the operation amount, such as the pulse motor or the direct drive motor. Truck movement amount detection means 98 for detecting an amount in which the truck 37 is moved is mounted on the other driving wheel 26. The detection means can be realized by means measuring a traveling distance or speed used in an automobile or bicycle. The truck movement amount detection means 98 for driving both the driving wheels 26 by the motor 96 to detect an amount in which the truck 37 is moved may be mounted on the axis of the motor 96. The numeral 95 denotes a truck movement control part and receives a signal of the truck movement amount from the conveying mechanism control part 10 by wireless communication. It also transmits a signal of a truck movement amount detected by the truck movement amount detection means 98 to the data processing part 102 by wireless communication. The power of the motor 96, not shown, is supplied from a battery mounted on part of the truck 37.

FIG. 19C is a diagram showing the detail of an example of the truck movement control part 95 according to Embodiment 3. The truck movement control part 95 has communication unit 97 with the control part for controlling signal transmission/reception between the conveying mechanism control part 10 and the data processing part 102 and transmits a signal received from the conveying mechanism control part 10 via a control circuit part 41 to the driving motor 96. The signal of the truck movement amount detected by the truck movement amount detection means 98 is transmitted via the control circuit part 41 to the data processing part 102. The communication is also permitted by a wire method. To avoid trouble due to sagging of the cable during conveying, it is desirably realized by the wireless communication method.

Embodiment 3 is the same as Embodiments 1 and 2 explained in FIG. 3 except that the conveying mechanism is an automated truck. The entire system configuration of Embodiment 3 may be that shown in FIG. 1

Also in Embodiment 3, the growing case 13 can be guided on the monorail 25 to be moved to an arbitrary position on the table 93 to maintain a fixed posture and to be opposite the camera 15. While instructing the position of the conveying operation in detail, the conveying operation can be done. The conveying amount can be controlled for each growing case to realize image acquisition when cases of different shapes and observed plants having different growing stages are placed on the same table.

Figure 20A:
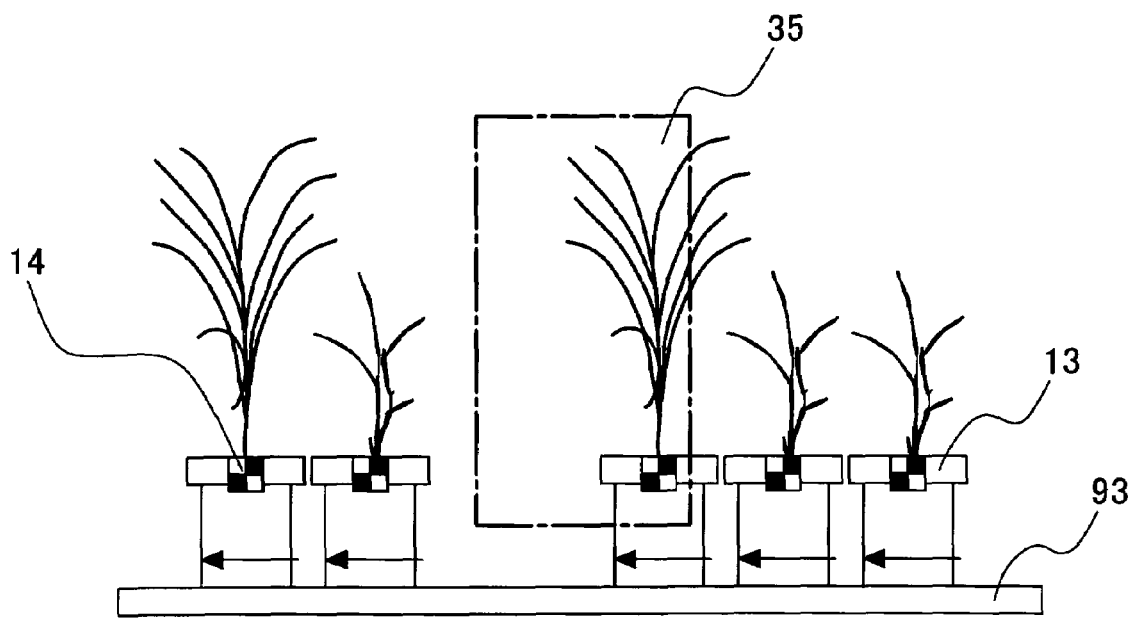
FIG. 20A is a diagram showing the state that observed plants in the growing cases 13 having different growing steps are conveyed on the table 93 in the arrow directions according to Embodiment 3.
Figure 20B:
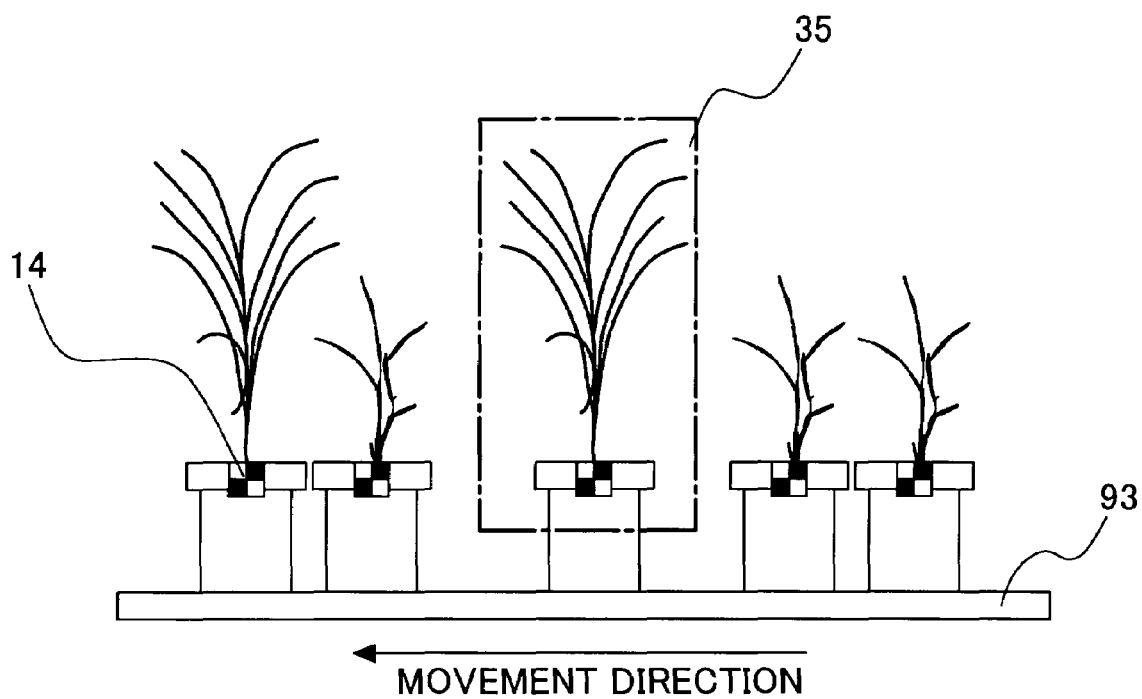
FIG. 20B is a diagram showing together the state that the noted growing case 13 is close to an image acquisition area from the state of FIG. 20A and the later controlled result.

FIGS. 20A and 20B are diagrams of assistance in explaining a specific example of conveying mechanism control according to Embodiment 3. As explained in FIGS. 19A to 19C, in Embodiment 3, the growing case 13 can be conveyed to an arbitrary position on the table 93. Detection for stopping opposite a predetermined position of the camera 15 is necessary.

FIG. 20A is a diagram showing the state that observed plants in the growing cases 13 having different growing steps according to Embodiment 3 are conveyed on the table 93 in the arrow directions. The operation is performed for each of the growing cases 13 according to the operation flow explained in FIG. 7. The position detecting marks 14 are attached to the growing cases 13. An area 35 surrounded by the chain line is a position correctly opposite the camera 15 and means an image acquisition area. While performing position detection of the position detecting mark 14, the conveying operation is performed until the growing case 13 is correctly stopped in the image acquisition area 35.

FIG. 20B is a diagram showing together the state that the noted growing case 13 is close to the image acquisition area 35 from the state of FIG. 20A and the later controlled result. In this example, in the state that the growing cases 13 shown in FIG. 20A are conveyed at the same time in the arrow direction, when detecting by position detection of the position detecting mark 14 that the noted growing case 13 is close to the image acquisition area 35, conveying of other growing cases is stopped to move only the noted growing case 13 to the image acquisition area 35.

When the noted growing case 13 is conveyed in the state that it is contacted with other growing cases 13, in the state that only the noted growing case 13 reaches the image acquisition area 35, the growing cases 13 on both sides are moved so that they are outside the image acquisition area 35. Such correction operation is performed so that only the noted growing case 13 is stopped in the center of the image acquisition area 35 and adjacent plants cannot be moved to the image in image acquisition. To simplify the control, the conveying may be scheduled so that a space is constantly left on the travel direction side of the noted growing case 13. Seeing the example of FIG. 20B, when the image acquisition of the noted growing case 13 is completed, the growing case 13 may be moved to the travel direction side for conveying all the growing cases 13.

Figure 21A:
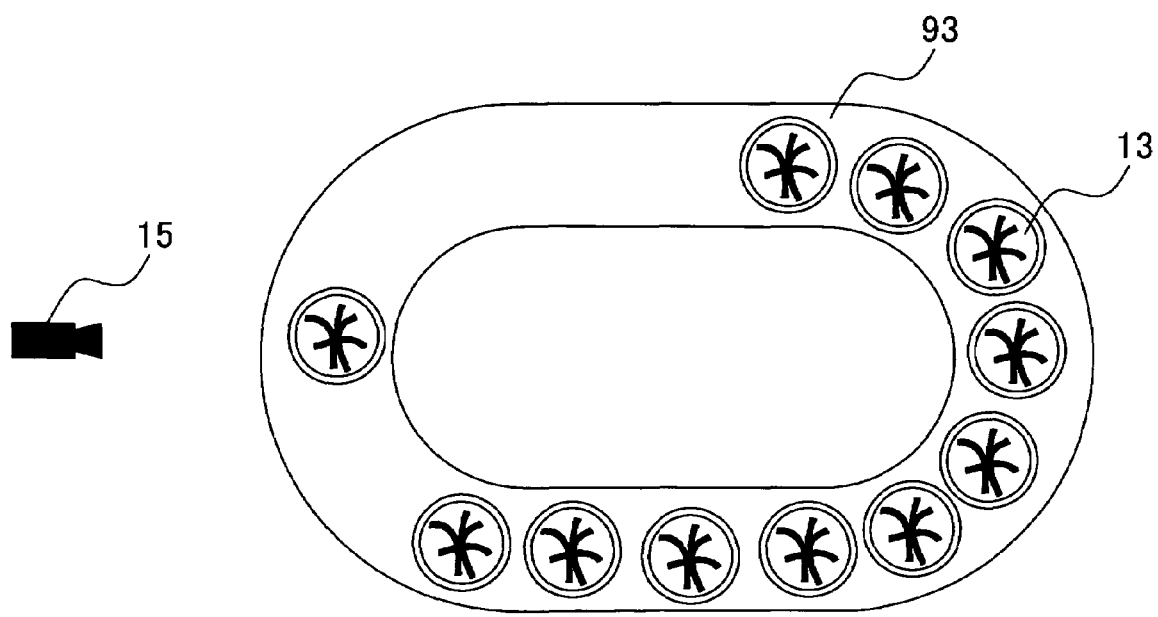
FIG. 21A is a diagram of assistance in explaining a conveying operation according to Embodiment 3 in the state that observed plant are middle seedlings.
Figure 21B:
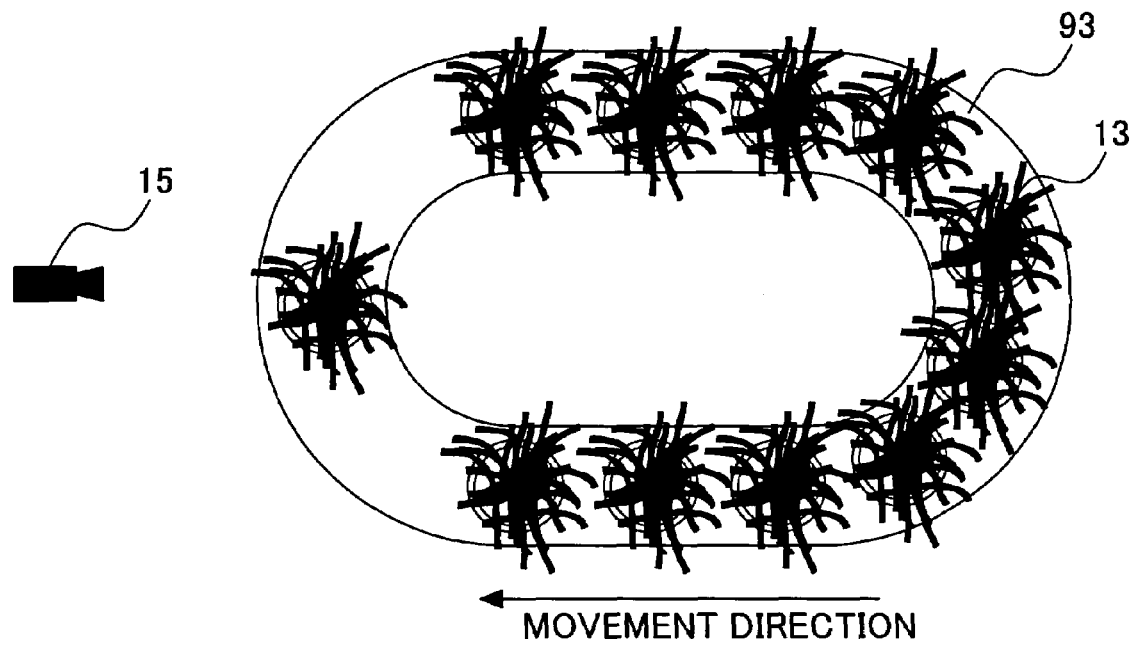
FIG. 21B is a diagram of assistance in explaining a conveying operation according to Embodiment 3 in the state that observed plants are mature.

FIGS. 21A and 21B are diagrams of assistance in explaining a conveying operation according to Embodiment 3 when observed plants are grown in their growing cases 13 from middle seedling to mature plant. FIG. 21A shows the conveying operation in the state that observed plants are middle seedlings, and FIG. 21B shows the conveying operation in the state that observed plants are mature. The drawings show the conveying table 93 seen from the top. In FIG. 21A, the growing cases 13 may be contacted with each other on the table 93. In FIG. 21B, the leaves of the observed plant are thick, which may inhibit the growing of the plants in the adjacent growing cases 13. The growing cases 13 must be arranged on the table 93 to be suitably apart from each other.

In Embodiment 3, the individual growing cases 13 can be independently moved. When the growing cases 13 in number in consideration of the growing step of the observed plants are initially arranged, no work reducing the number of the growing cases 13 according to growth is necessary. As shown in FIG. 21B, when the growing case 13 is opposite the camera 15, there may be a space for including only one growing case 13 in the image acquisition area 35, as shown in FIG. 20B, thereby permitting high-density growing.

In Embodiment 3, initially, there is no need to consider that the plants of the adjacent growing cases 13 are not included in the image acquisition area 35. To shorten time for image acquisition of all the growing cases 13 on the table 93, conveying time must be shortened. The space between the growing cases 13 is smaller to reduce the conveying amount after image acquisition to shorten the conveying time, which is effective. As shown in FIG. 20B, when moving only the noted growing case 13 to the image acquisition area 35 by the position detection of the position detecting mark 14, part of the image of the plants in the adjacent growing cases 13 may be included in the area 35.

Figure 22A:
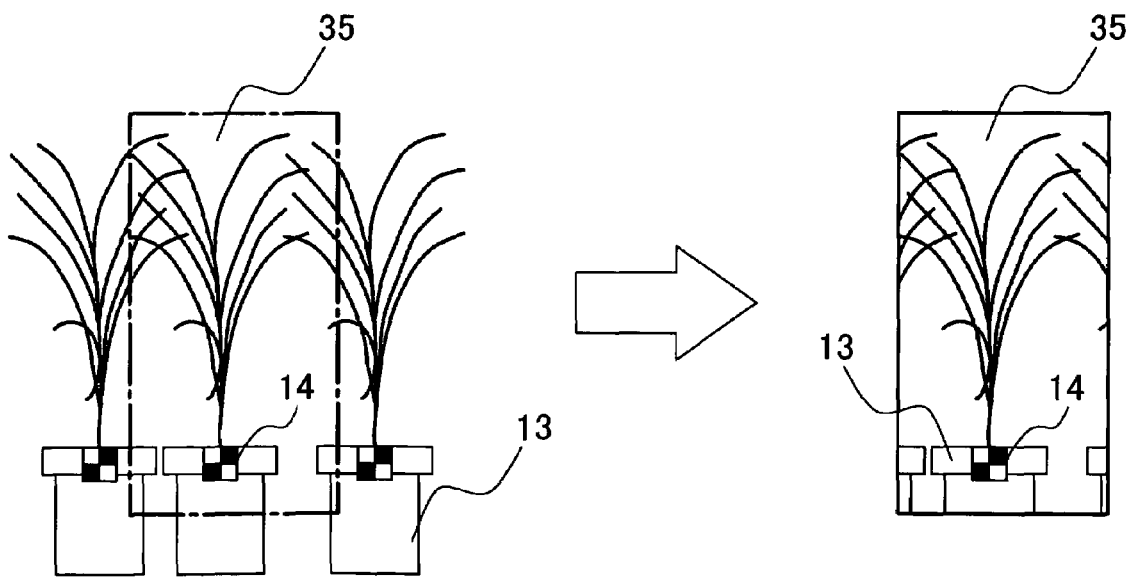
FIG. 22A is a diagram showing an example according to Embodiment 3 in which image acquisition is performed in the state that part of images of the plants in the adjacent growing cases 13 is included in an area 35.

FIG. 22A is a diagram showing an example in which image acquisition is performed in the state that part of images of the plants in the adjacent growing cases 13 is included in the area 35. As shown on the left side of FIG. 22A, image acquisition is performed in the state that a predetermined relation between the position detecting mark 14 of the noted growing case 13 with the area 35 can be detected. As shown on the left side of FIG. 22A, in the image acquisition, part of the thick leaves of the plants in the adjacent growing case 13 is included.

Figure 22B:
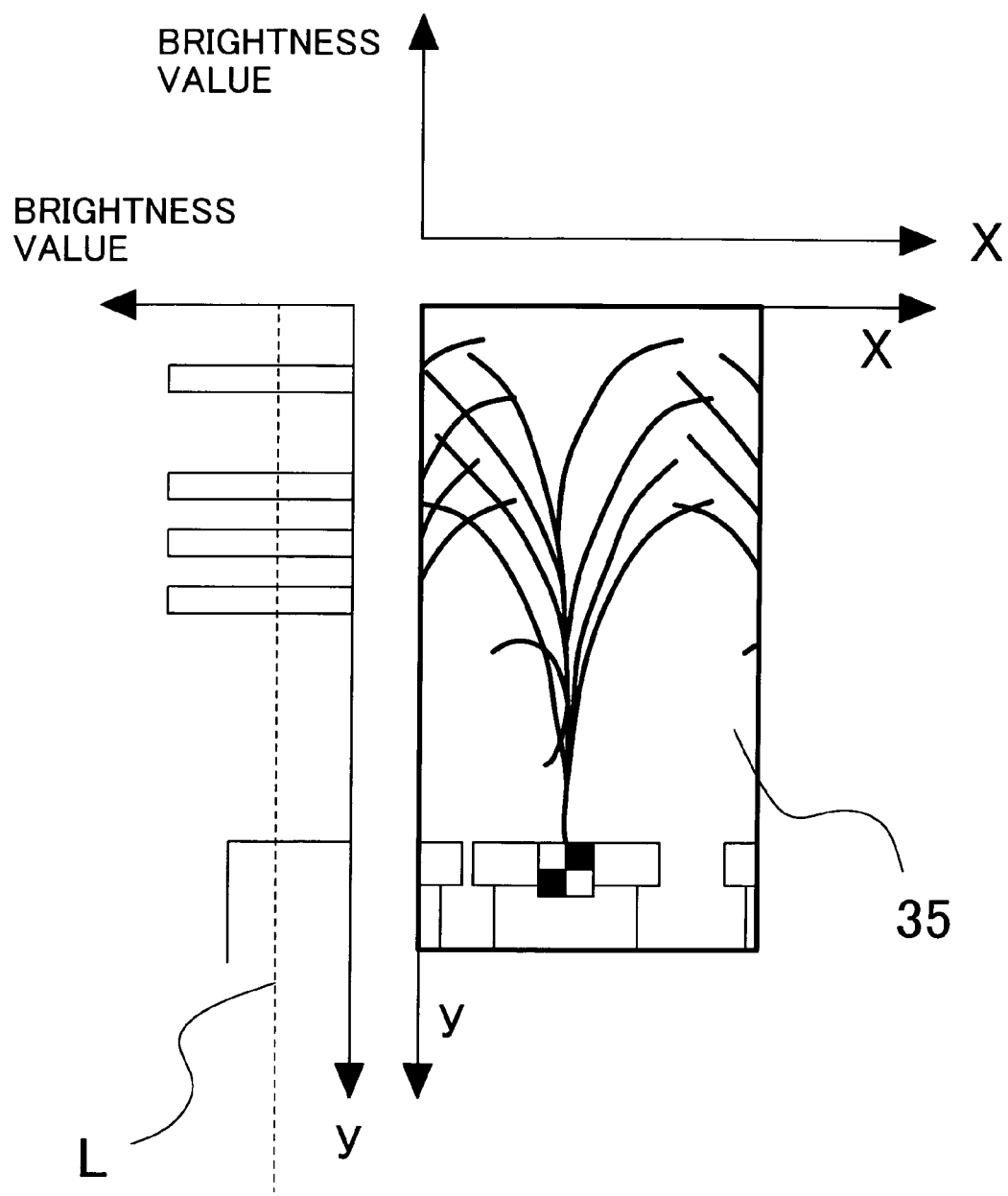
FIG. 22B is a diagram of assistance in explaining an example of determination processing according to Embodiment 3 for detecting the state that part of thick leaves of the plants in the adjacent growing cases 13 is included.

FIG. 22B is a diagram of assistance in explaining an example of determination processing for detecting the state that part of thick leaves of the plants in the adjacent growing cases 13 is included. The brightness values of the boundary part of the acquired image shown on the right side of FIG. 22A are referred to determine whether the adjacent plants are included or not. As shown in the drawing, changes in the brightness value on the boundary is plotted on the x-axis and the y-axis in the boundary part of the acquired image. When there is no image element on the boundary, the brightness value is 0. When there is an image element thereon, the brightness value is above a certain level. The threshold value of detection of the brightness value is L for determination. When the brightness value exceeding the L is detected, part of thick leaves of the plants in the adjacent growing cases 13 is determined to be included. When detection of the brightness value is performed on both sides of the boundary side of the acquired image, according to the determined result, the conveying of only the growing case 13 on the travel direction side is advanced, the growing case 13 on the opposite side of the travel direction is conveyed in the reverse direction, or the conveying control of both is performed to acquire an image not including part of thick leaves of the plants in the adjacent growing cases 13. While shortening conveying time, an image of a constantly fixed plant can be acquired to increase the measurement accuracy in shape measurement. The determined value of image detection is desirably decided in the previous test operation since it depends on an environment such as image acquisition illumination condition. Image acquisition is performed while determining the adjacent plants, thereby constantly performing image acquisition of only a target plant.

In all the above-described embodiments, giving an ID for specifying the growing case 13 is not mentioned. Display for an ID may be given in the form that the position detecting mark 14 is attached to the upper, lower, left or right sides of the growing cases 13. Information on the growing case 13 can be acquired to be matched with information on the position mark, which is useful for management.

As described above, there can be provided a system which, in an image of changes in growing in a plant growing process, can reduce a measurement error caused by an operation error of the conveying mechanism with high accuracy to realize the growing comparison and the growing analyzing of many plants with high accuracy. There can be provided means efficiently realizing the growing analyzing of the acquired growing images of many plants.

The image acquisition system and the analyzing method of the present invention are effective for accommodating, into the growing case, changes in growing of a living body other than a plant or changes in the synthesis reaction of chemical substances included in the growing case of the image acquisition system to analyze its chronological shape changes. For example, it can be applied such that the internal organ, blood vessel or cells of an animal or a human is accommodated into the growing case to acquire an image of the growing state by the image acquisition system of the present invention to analyze from the image the growing speed of the blood vessel or changes in the shape of the internal organ or cells by the analyzing method of the present invention. It can be applied to changes in generated shape in a chemical synthesis reaction such as plastic.

What is claimed is:

1. An observed object growing analyzing system comprising:
    a plurality of cases for growing observed objects;
    conveying means for conveying said plurality of cases;
    image acquisition means outputting electronic image information on the observed objects in said plurality of cases;
    means processing an image acquired by said image acquisition means;
    first storing means temporarily storing a processed result by said image processing means;
    means controlling a conveying amount for evaluating based on said temporarily stored result whether the conveying amount of said case is suitable or not, and when determining it is not suitable, correcting position of said case; and
    second storing means acquiring electronic image information on the observed objects in said plurality of cases again by said image acquisition means in the corrected case position and storing image information acquired again and image information when determining the conveying amount of said case is suitable
    image acquisition means capable of outputting electronic image information on the operation state of the conveying means for conveying said plurality of cases; and
    means evaluating based on the result obtained by image processing said image acqiuired by said image acquisition means whether the operation of said case conveying means is suitable or not, and when it is not suitable, displaying or giving an alarm of it.

2. The observed object growing analyzing system according to claim 1, further comprising means sequentially displaying image information stored in said second storing means.

3. The observed object growing analyzing system according to claim 1, wherein a deviation amount of part of a plant is obtained from image information stored in said second storing means, and changes in the deviation amount with time are converted into numbers to be applied to growing analyzing of the plant.

4. The observed object growing analyzing system according to claim 1, wherein the conveying means for conveying said plurality of cases conveys said cases on the rotation track and allows the same case to be opposite said image acquisition means for each rotation.

5. The observed object growing analyzing system according to claim 4, wherein said image acquisition means acquiring an image after said case is conveyed to the position opposite said image acquisition means and a predetermined time elapses.

6. An observed object growing analyzing system comprising:
    a plurality of cases for growing observed objects;
    conveying means for conveying said plurality of cases;
    image acquisition means outputting electronic image information on the observed objects in said plurality of cases and position detecting mark on each of said plurality of cases;
    means processing an image acquired by said image acquisition means;
    first storing means temporarily storing a processed result by said image processing means; means controlling a conveying amount for evaluating based on said temporarily stored result whether the conveying amount of said case is suitable or not, and when determining it is not suitable, correcting position of said case; and
    second storing means acquiring electronic image information on the observed objects in said plurality of cases again by said image acquisition means in the corrected case position and storing image information acquired again and image information when determining the conveying amount of said case is suitable
    image acquisition means capable of outputting electronic image information on the operation state of the conveying means for conveying said plurality of cases; and
    means evaluating based on the result obtained by image processing said image acquired by said image acquisition means whether the operation of said case conveying means is suitable or not, and when it is not suitable, displaying or giving an alarm of it.

7. The observed object growing analyzing system according to claim 6, further comprising means sequentially displaying image information stored in said second storing means.

8. The observed object growing analyzing system according to claim 6, wherein a deviation amount of part of a plant is obtained from image information stored in said second storing means, and changes in the deviation amount with time are converted into numbers to be applied to growing analyzing of the plant.

9. The observed object growing analyzing system according to claim 6, wherein the conveying means for conveying said plurality of cases conveys said cases on the rotation track and allows the same case to be opposite said image acquisition means for each rotation.

10. The observed object growing analyzing system according to claim 9, wherein said image acquisition means acquiring an image after said case is conveyed to the position opposite said image acquisition means and a predetermined time elapses.

11. An observed object growing analyzing system comprising:
    a plurality of cases for growing observed objects;
    a plurality of conveying means for placing each of said plurality of cases and automatically conveying it;
    image acquisition means outputting electronic image information on the observed objects in said plurality of cases;
    means processing an image acquired by said image acquisition means;
    first storing means temporarily storing a processed result by said image processing means;
    means controlling a conveying amount for evaluating based on said temporarily stored result whether the conveying amount of said case is suitable or not, and when determining it is not suitable, correcting position of said case; and
    second storing means acquiring electronic image information on the observed objects in said plurality of cases again by said image acquisition means in the corrected case position and storing image information acquired again and image information when determining the conveying amount of said case is suitable image acquisition means capable of outputting electronic image information on the operation state of the conveying means for conveying said plurality of cases; and means evaluating based on the result obtained by image processing said image acquired by said image acquisition means whether the operation of said case conveying means is suitable or not, and when it is not suitable, displaying or giving an alarm of it.

12. The observed object growing analyzing, system according to claim 11, wherein said plurality of conveying means for automatic conveying travel on a predetermined route by guiding means provided on a plane and said conveying means are controlled by a conveying control signal transmitted by a wireless method.

13. The observed object growing analyzing system according to claim 12, wherein the guiding means conveys said case on the rotation track and allows the same case to be opposite said image acquisition means for each rotation.

14. The observed object growing analyzing system according to claim 13, wherein said image acquisition means acquiring an image after said case is conveyed to the position opposite said image acquisition means and a predetermined time elapses.

15. The observed object growing analyzing system according to claim 11, further comprising means sequentially displaying image information stored in said second storing means.

16. The observed object growing analyzing system according to claim 11, wherein a deviation amount of part of a plant is obtained from image information stored in said second storing means, and changes in the deviation amount with time are converted into numbers to be applied to growing analyzing of the plant.

17. The observed object growing analyzing system according to claim 11, wherein noting data on the boundary of said image acquired by said image acquisition means, whether the position of the case opposite said image acquisition means is suitable or not is evaluated.

* * * * *